United States Patent [19]

Bittle et al.

[11] Patent Number: 4,769,237

[45] Date of Patent: Sep. 6, 1988

[54] SYNTHETIC PICORNAVIRUS ANTIGEN

[76] Inventors: James L. Bittle, 5353 Calle Vista, San Diego, Calif. 92109; Richard A. Lerner, 7750 Roseland, La Jolla, Calif. 92037

[21] Appl. No.: 653,475

[22] Filed: Sep. 20, 1984

Related U.S. Application Data

[63] Continuation of Ser. No. 478,847, Mar. 25, 1983, abandoned, which is a continuation-in-part of Ser. No. 368,308, Apr. 14, 1982, abandoned, which is a continuation of Ser. No. 682,819, Dec. 18, 1984, Pat. No. 4,544,500.

[51] Int. Cl.⁴ .................. A61K 39/00; C07K 37/02
[52] U.S. Cl. .................................... 424/88; 530/323; 530/326; 530/806
[58] Field of Search .............. 530/317, 323, 326, 322, 530/403, 806, 345, 404; 935/65; 424/89

[56] References Cited

U.S. PATENT DOCUMENTS

| | | | |
|---|---|---|---|
| 4,102,877 | 7/1978 | Nutt | 530/317 |
| 4,140,763 | 2/1979 | Bachrach et al. | 424/89 |
| 4,544,500 | 10/1985 | Bittle et al. | 530/806 X |

FOREIGN PATENT DOCUMENTS

| | | | |
|---|---|---|---|
| 68693 | 5/1983 | European Pat. Off. | 424/89 |
| 2079288 | 1/1982 | United Kingdom | 424/89 |

OTHER PUBLICATIONS

Stanway et al., Proc. Natl. Acad. Sci USA, vol. 81, pp. 1539–1543 (1984).
Boothroyd et al., Nature, vol. 290, pp. 800–802 (1981).
Kitamura et al., Nature, vol. 290, pp. 547–553, (1981).
Racaniello et al., Proc. Natl. Acad. Sci. USA, vol. 78, pp. 4887–4891, (1981).
Hopp et al., Proc Natl. Acad. Sci. USA, vol. 78, pp. 3824–3828, (1981).
Nomoto et al., Proc. Nat. Acad. Sci. USA, vol. 79, pp. 5793–5797 (1982).
Strohmaier et al., J. Gen Virol., vol. 59, pp. 295–306, (Apr. 1982).
Meloen et al., J. Gen. Virol., vol. 45, pp. 761–763, (1979).
Sutcliffe et al., Nature, vol. 287, pp. 801–805, (1980).
Marglin et al., Ann. Rev. Biochem., 39: 841–866 (1970).
Bittle et al., Nature, 298: 30–33, Jul. 1982.
Emini et al. (1983) *Nature,* 304:699–703.
Emini et al. (1983) *Vaccines* 84:65–75.
Chow et al. (1985) *Proc. Natl. Acad. Sci. USA,* 82:910–914.
Diamond et al. (1985) *Science,* 229:1090–1093.
Rossmann et al (1985) *Nature,* 317:145–153.
Hopp and Woods (1983) *Mol. Immunol.,* 20:483–489.
Atassi and Webster (1983) *Proc. Natl. Acad. Sci. USA.,* 80:840–844.
Emini et al. (1982) *J. Virol.,* 43:997–1005.
Stanway et al., (1983) *Nature,* 301:674–679.

*Primary Examiner*—Delbert R. Phillips
*Attorney, Agent, or Firm*—Dressler, Goldsmith, Shore, Sutker & Milnamow Ltd.

[57] ABSTRACT

A specific synthetic antigenic peptide that contains a sequence of about 20 amino acid residues corresponding to a certain region of the antigenic picornavirus capsid protein such as the VP1 capsids of foot-and-mouth disease and poliomyelitis viruses. That region is located at a distance of about 60 to about 75 percent of the total amino acid length measured from the amino-terminus. Specific synthetic peptide-containing vaccines that produce antibodies that protect animal hosts from the picornaviruses, as well as antibodies to and diagnostics for Picornavirus antigens are disclosed.

27 Claims, 2 Drawing Sheets

FIG. 1

AMINO ACID RESIDUE SEQUENCES OF EIGHT
FMDV $VP_1$ CAPSID PROTEINS AT POSITIONS 130-160

```
          130                              140
O1k   TyrAsnGlyGluCysArgTyrAsnArgAsnAlaValProAsnLeu
O1c   TyrAsnGlyGluCysArgTyrSerArgAsnAlaValProAsnVal
A10   TyrAspGlyThrAsnLysTyrSerAlaSerAspSer -  - Arg
A12   TyrAsnGlyThrAsnLysTyrSerAlaSerGlySerGly - Val
A24   TyrAsnGlyThrSerLysTyrAlaValGlyGlySerGly - Arg
A27   TyrAsnPheThrAsnLysTyrSerAsnGlyGlyGln  -  - Arg
A79   TyrAsnGlyThrSerLysTyrThrValGlyGlySerGly - Arg
C3    TyrThrGlyThrThrThrTyrThrThrSerAla  -  -  - Arg 150                              160
O1k   ArgGlyAspLeuGlnValLeuAlaGlnLysValAlaArgThrLeuPro
O1c   ArgGlyAspLeuGlnValLeuAlaGlnLysValAlaArgThrLeuPro
A10   SerGlyAspLeuGlySerIleAlaAlaArgValAlaThrGlnLeuPro
A12   ArgGlyAspPheGlySerLeuAlaProArgValAlaArgGlnLeuPro
A24   ArgGlyAspMetGlyThrLeuAlaAlaArgValValLysGlnLeuPro
A27   AlaGlyAspMetGlySerLeuAlaAlaArgValAlaLysGlnLeuPro
A79   ArgGlyAspMetGlySerLeuAlaAlaArgValAlaLysGlnLeuPro
C3    ArgGlyAspLeuValHisLeuAlaAlaAlaHisAlaArgHisLeuPro
```

FIG. 2

AMINO ACID RESIDUE SEQUENCES OF POLIO VIRUS VP$_1$
CAPSID PROTEINS AT POSITIONS 61-82 AND 182-201

```
           61
Type 1    ValGlnThrArgHisValValGlnHisArgSerArgSerGluSer
Type 3    ValGlnThrArgHisValValGlnArgArgSerArgSerGluSer
           80
SerIleGluSerPhe
ThrIleGluSerPhe
           182
Type 1    SerIlePheTyrThrTyrGlyThrAlaProAlaArgIleSer
Type 3    SerIlePheTyrThrTyrGlyAlaAlaProAlaArgIleSer
           201
ValProTyrValGlyIle
ValProTyrValGlyLeu
```

SYNTHETIC PICORNAVIRUS ANTIGEN

CROSS-REFERENCE TO RELATED APPLICATION

This is a continuation of application Ser. No. 478,847 filed Mar. 25, 1983 and now abandoned, that was a continuation-in-part of U.S. application Ser. No. 368,308 filed Apr. 14, 1982, now abandoned, and its continuation application Ser. No. 682,819 filed Dec. 18, 1984, now U.S. Pat. No. 4,544,500.

TECHNICAL FIELD

The present invention relates to vaccines and antigens for infectious disease and, more specifically, to antigens useful in the diagnosis and treatment of diseases caused by viruses of the family Picornavirus such as foot-and-mouth disease and poliomyelitis.

BACKGROUND

Foot-and-mouth disease is a highly contagious disease of great economic importance, afflicting primarily cloven-hoofed animals. The mortality directly attributable to foot-and-mouth disease is comparatively low, generally, but in young animals the mortality can be quite high. Of greater economic importance, the disease is so debilitating that infected animals cannot be raised and fed economically. The only recognized effective procedure for eliminating the infection once it has been discovered is to destroy all infected animals, disinfect all premises which have been occupied by the animals, and decompose the carcasses in quicklime. Since the infection spreads extremely rapidly, the economic foundation of entire communities or regions can be destroyed by one major outbreak of foot-and-mouth disease.

Vaccines have been produced which immunize against foot-and-mouth disease, primarily, by inactivation or attenuation of the virus. Such vaccines have been found to be effective in some measure, but outbreaks of foot-and-mouth disease have been linked to vaccines in which the virus was incompletely inactivated or insufficiently attenuated as well. Infections have also been traced to the escape of virus from facilities devoted to research on foot-and-mouth disease or to production of foot-and-mouth disease vaccines.

Foot-and-mouth disease (FMD) is cuased by a Picornavirus of the genus aphthovirus. There are several viral serotypes of foot-and-mouth disease virus (FMDV), the most common of which are identified by the serotype designation A, O and C, and less common identified as SAT-1, SAT-2, SAT-3 and ASIA-1. Among these serotypes, several subtypes and subtype strains have also been identified. The following are among the identified subtypes and subtype strains: FMDV A, subtype 10, strain 61 and subtype 12, strains 119, USA and Pirbright; FMDV 0, subtype 1, strain Kaufbeuren; and FMDV C, subtype 3, strain Indaial.

FMDV has been described in some detail; see, for example, H. L. Backrach, in *Beltsville Symposium on Agricultural Research*, J. A. Romberger, Ed., Allanheld, Montclair, N.J. 1977), pp. 3–32; Annual Reviews of Microbiology, 22, 201 (1968). The molecular biology of these viruses have been described, R. R. Rueckert, in *Molecular Biology of Picornavizuses*, R. Perex-Bercoff, Ed. Plenum, New York, (1979), p. 113. The virus has a molecular size of about $7 \times 10^6$ daltons and contains a plus-stranded RNA genome of approximately 8,000 nucleotides. Picornavirus proteins have been synthesized in infected cells as a precursor of a protein that is subsequently processed by cellular and virus-coded proteases into four major capsid proteins ($VP_1$, $VP_2$, $VP_3$, and $VP_4$) and numerous non-capsid proteins.

The whole $VP_3$ protein when used to inoculate swine elicited a neutralizing anti-body response and protected both swine and cattle from infection. [J. Laporte, et al., *C.R. Acad. Sci.*, 276: 3399 (1973); H. L. Backrach, et al., *J. Immunol.*, 115: 1636 (1975). See also U.S. Pat. No. 4,140,763.] Based upon this information, Dennis G. Kleid, et al. *Science*, 214: 1125–1129 (Dec. 4, 1981), were able to produce a cloned viral protein vaccine for foot-and-mouth disease which gave antibody responses in cattle and swine.

It is noted that the literature in this field utilizes the same names to refer to different capsid proteins. Thus, the above-mentioned workers in the United States typically refer to the capsid protein referred to herein and in Europe as $VP_1$, as the $VP_3$ capsid. There is agreement, however, that the capsid protein referred to herein as $VP_1$, and referred to by others as $VP_3$, is the immunologically active capsid protein.

Recombinant DNA molecules and processes for producing peptides with the specificity of foot-and-mouth disease viral antigens are described in United Kingdom Patent Application GB No. 2,079, 288A, Jan. 20, 1982. See also Boothroyd et al, *Nature*, 290: 800–802 (1981); Kleid et al., *Science*, 214: 1125–1129 (1981); and EPO Publication Number 0 068 693 2A corresponding to application number 82303040.8 filed 11.06.82.

K. Strohmaier et al., Proc. 5th Int. Congress Virology, Strasbourg, 1981, poster session, have digested the $VP_1$ protein (denominated $VP_{Thr}$ therein) with enzymes as well as cyanogen bromide, and raised neutralizing antibodies using the peptide fragments of those digests. Those authors suggested that the amino acid residue sequences at postions 146 through 155 and 200 through 213 from the protein amino-terminus induced production of immunologically important antibodies. Those authors also suggested that amino acid residue sequences at positions 141 through 145 and 155 through 161 were among the regions of inactive, non-inducing peptides. This $VP_1$ sequence corresponds to the $VP_3$ sequence described earlier in the United States; see explanation by Meloen, A. H., *J. Gen. Virol*, 45:761–763 (1979).

A full paper by Strohmaier et al., *J. Gen. Virol.*, 59:295–306 (1982), detailed the work reported at the above poster session, and provides a correlation for the various capsid protein nomenclatures utilized by workers in this field. This paper reiterated the findings reported at the poster session that two cyanogen bromide cleavage products termed $CB_1$ and $CB_2$ and an enzyme cleavage product termed $A_2$ of $VP_1$ which correspond to amino acid residue positions 55–180, 181–213, and 146–213, respectively, from the amino-terminus, produced neutralizing antibodies. This paper also reiterated that regions of overlap with other cleavage products, including regions 141–145 and, 155–161, had no apparent effect. Those authors stated, at page 303, that they though it "likely that only two small regions are essential for the immunizing potency of the protein . . . "

The poliomyelitis (hereinafter polio) and Hepatitis A viruses are also members; i.e. genera, of the Picornavirus family. Successful vaccines against types 1, 2 and 3 polio viruses have been used since the 1950's, while no successful vaccine against Hepatitis A is known.

One of the distinguishing features of the Picornaviruses is that they contain four capsid proteins. The capsid protein denominated $VP_1$ of polio type 1 has been found to contain an antigenic determinant region capable of inducing production of antibodies that neutralize the virus, although heretofore the specific amino acid determinant regions of the $VP_1$ capsid have not been found. A specific capsid of the Hepatitis A virus has not yet been identified as being responsible for inducing production of neutralizing antibodies.

The antipolio vaccines typically utilize inactivated types 1, 2 and 3 viruses. In some instances, all of the allegedly killed viruses have not been killed, or the virus particles have not been sufficiently attenuated, so that about one out of one million innoculations causes an inoculated person to contract clinical disease.

It would therefore be beneficial if an antipolio vaccine could be prepared that is free from any possibility of containing a live or even attenuated virus. It would also be beneficial if a useful antipolio vaccine could be prepared that is free from celluar debris, bacterial endotoxins and growth medium by-products as are frequently present in vaccine preparations obtained from recombinant DNA technology, as is discussed hereinafter. It would be still more beneficial if vaccines and diagnostic products could be found that were safe and highly effective.

In the past antigens have been obtained in several fashions, including derivation from natural materials, coupling of a hapten to a carrier, and by recombinant DNA technology Sela, et al., *Proc. Nat. Acad. Sci., U.S.A.*, 68:1450–1455 (July, 1971); *Science*, 166:1365–1374 (December 1960); *Adv. Immun.*, 5:29–129 (1966) have also described certain synthetic antigens.

Antigens derived from natural materials are the countless number of known antigens which occur naturally, such as blood group antigens, HLA antigens differentiation antigens, viral and bacterial antigens, and the like. Considerable effort has been expended over the last century in identifying and studying these antigens.

Certain "synthetic" antigens have been prepared by coupling small molecules to carriers such as, for example, bovine serum albumin, thus producing antigens which will cause production of antibody to the coupled small molecule. The carrier molecule is necessary because the small molecule itself would not be "recognized" by the immune system of the animal into which it was injected. This technique has also been employed in isolated instances to prepare antigens by coupling peptide fragments of known proteins to carriers, as described in the above-referenced Sela et al. articles.

While this hapten-carrier technique has served the research community well in its investigations of the nature of the immune response, it has not been of significant use to produce antigens which would play a role in diagnostic or therapeutic modalities. The reasons for this deficiency are several.

First, to choose and construct a useful antigenic determinant from a pathogen by this technique, one must determine the entire protein sequence of the pathogen to have a reasonable chance of success. Because of the difficulty of this task it has rarely, if ever, been done Classically, vaccines are manufactured by introducing killed or attenuated organisms into the host along with suitable adjuvants to initiate the normal immune response to the organisms while, desirably, avoiding the pathogenic effects of the organism in the host. The approach suffers from the well known limitations in that it is rarely possible to avoid the pathogenic response because of the complexity of the vaccine which includes not only the antigenic determinant of interest but many related and unrelated deleterious materials, any number of which may, in some or all individuals, induce an undesirable reaction in the host.

For example, vaccines produced in the classical way may include competing antigens which are detrimental to the desired immune response, antigens which include unrelated immune responses, nucleic acids from the organism or culture, endotoxins and constituents of unknown composition and source. These vaccines, generated from complex materials, inherently have a relatively high probability of inducing competing responses even from the antigen of interest. In addition, such known vaccines against FMDV must be kept refrigerated prior to use, and refrigeration in remote areas where the vaccines are used is often difficult to obtain.

Recombinant DNA technology has opened new approaches to vaccine technology which does have the advantage that the manufacture begins with a monospecific gene; however, much of this advantage is lost in actual production of antigen in *Escherichia coli*, or other micro organisms. In this procedure, the gene material is introduced into a plasmid which is then introduced into *E. coli* which produces the desired protein, along with other products of the metabolism, all in mixture with the nutrient. This approach is complicated by the uncertainty whether the desired protein will be expressed in the transformed *E. coli*.

Further, even though the desired protein may be produced, there is uncertainty as to whether or not it can be harvested, or whether it will be destroyed, in the process of *E. coli* growth. It is well known, for example, that foreign or altered proteins are digested by *E. coli*. Even if the protein is present in sufficient quantities to be of interest, it must still be separated from all of the other products of the *E. coli* metabolism, including such deleterious substances as undesired proteins, endotoxins, nucleic acids, genes and unknown or unpredictable substances.

Finally, even if it were possible, or became possible through advanced, though necessarily very expensive, techniques, to separate the desired protein from all other products of the *E. coli* metabolism, the vaccine still comprises an entire protein which may include undesirable antigenic determinants, some of which are known to initiate very serious, adverse responses. Indeed, it is known that certain proteins which could otherwise be considered as vaccines include an antigenic determinant which induces such serious cross reference or side reactions as to prevent the use of the material as a vaccine.

It is also possible, using hybridoma technology, to produce antibodies to viral gene products. Basically, hybridoma technology allows one to begin with a complex mixture of antigens and to produce monospecific antibodies later in the process. In contrast, the present invention is the reverse process, in that it starts with the ultimate in high purity antigenic determinant and thus avoids the necessity for purification of the desired antigenic product.

Hybridoma antibodies are known to be of low avidity and low binding constant, and therefore, have limited value.

Ultimately, in hybridoma technology, one must rely on the production of the antibody by cells which are malignant, with all of the attendant concerns regarding separation techniques, purity and safety.

Hybridoma production relies upon tissue culture or introduction into mice, with the obvious result that production is costly; there is also inherent variability from lot to lot.

In addition, it is difficult to make a hybrid to molecules which comprise only a small percentage of the complex mixture one must start with.

Previous studies by Arnon et al., *Proc. Nat. Acad. Sci. U.S.A.* 68:1450 (1971), Atassi, *Immunochemistry* 12:423 (1975) and Vyas et al., *Science* 178:1300 (1972) have been interpreted by those authors to indicate that short linear amino acid sequences are, in general, unlikely to elicit antibodies reactive with the native protein structure. It was though that for most regions of most molecules, antigenic determinants resulted from amino acid residues well separated in the linear sequence but conformation of the peptides used to elicit antibodies was thought to be critical in most cases, even for those antigens involving amino acides close together in a sequence. Lerner, et al., *Cell* 23:109-110, (1981); *Nature* 287:801-805 (1980), discovered that antibodies to linear peptides react with native molecules. Elaborate biosyntheses thus become unnecessary, uneconomical and obsolete.

Nothwithstanding the availability of inactivated or attenuated virus vaccines against foot-and-mouth disease, there has remained a great economic and practical demand for, and great theoretical interest, in the development of a vaccine against foot-and-mouth disease which would be free of the risks which have heretofore attended the manufacture and handling of the FMDV which causes the disease. The availability of cloned viral proteins may well be a very significant step forward from the older and very risky approaches.

However, the cloned viral protein vaccine approach also carried with it a number of inherent disadvantages, limitations and risks. Variations in the biosynthesis system itself may cause variation in expression of proteins, thus affecting purity, yields, potency, etc. of antigens. In addition, the presence of other proteins, and difficult and inefficient separations, suggest the likelihood that vaccines produced through the cloned viral protein route will not be monospecific. Thus, purity, potency, and safety are major concerns with products derived from this technology.

Nothwithstanding that the general concept of preparing synthetic antigens, starting either from a known peptide sequence or from a genome have been described, and notwithstanding that the synthesis of peptides of suitable length for use in antigenic materials is now quite well known, there remains a very large area of antigen-antibody technology which continues to defy predictabilty. While there are some guidelines and some suggestions as to possible antigenic sequences, the field remains largely a matter of speculation, and of trial and error. Even with the recognition that a long sequence may contain antigenicaly active constituents, there remains a great deal of uncertainty and speculation as to whether all or only part of the sequence is required for antigenicity, and whether or not a smaller portion of the sequence would be of greater or lesser antigenicity.

BRIEF SUMMARY OF THE INVENTION

A specific synthetic, antigenic peptide containing a sequence of about twenty amino acid residues is contemplated by the present invention. This antigenic peptide includes an amino acid residue sequence that corresponds to a certain region of the antigenic Picornavirus capsid protein. That region is located at a distance equal to about 60 to about 75 percent of the total amino acid residue sequence length of the antigenic capsid protein as measured from the amino-terminus thereof. This peptide, when linked to a keyhole limpet hemocyanin carrier as a conjugate and introduced in an effective amount as a vaccine into a host animal, is capable of inducing production of antibodies in the host that immunoreact with the Picornavirus and protect the host from infection caused by that Picornavirus. The peptide preferably has a net positive ionic charge, exclusive of ionic charges of terminal peptide amino and/or carboxyl groups.

In another embodiment, this invention contemplates a synthetic, antigenic peptide containing a sequence of about twenty amino acid residues corresponding to an amino acid residue sequence from about position 130 to about 160 from the amino-terminus of the FMDV $VP_1$ capsid protein, and more particularly, from about positions 141 to about 160 is disclosed. This peptide, when linked to a keyhole limpet hemocyanin carrier as a conjugate and introduced in an effective amount as a vaccine into an animal host, is capable of inducing production of antibodies in the host that immunoreact with the foot-and-mouth virus and protect the host from infection caused by that virus.

In yet another embodiment, this invention provides synthetic, antigenic peptides each containing sequence of about twenty amino acids corresponding to amino acid sequences from about positions 61 to about 80 and from about position 182 to about 201, respectively, from the amino-terminus of the polio virus $VP_1$ capsid protein. Each of those peptides when individually linked to a keyhole limpet hemocyanin carrier as a conjugate and introduced in an effective amount into separate host animals is capable of inducing production of antibodies that immunoreact with polio virus and protect those animals from polio infections.

The synthetic antigenic peptides of this invention can be used along with physiologically acceptable diluents such as water and/or adjuvants in a vaccine that is capable of protecting animals from Picornavirus-induced diseases such as foot-and-mouth disease, or for raising antibodies useful in detecting the presence of antigenic proteins associated with Picornavirus-induced diseases.

A preferred sequence of about twenty amino acid residues of the foot-and-mouth disease-related synthetic peptide in the amino acid residue position region of about 130 to about 160 is selected from an amino acid residue sequence that corresponds to the amino acid residues of the sequence, written from left to right and in a direction from amino-terminus toward carboxy-terminus, shown below:

toward carboxy-terminus, shown below:
(130)
TyrAsn(Asp or Thr)Gly(Phe)Glu(Thr)Cys(Ser or Asn or Thr)Arg(Lys or Thr)TyrAsn(Ala or Ser or Thr)Arg(Val or Ala or Asn or Thr)Asn(Gly or Ser)
(140)
Ala(Asp or Gly)Val(Ser or Gln or X)Pro(Gly or Y)Asn(Z)Leu(Arg or Val)Arg(Ser or Ala)GlyAspLeu(Met or Phe)Gln(Gly)
(150)
Val(Thr or Ser or His)Leu(Ile)AlaGln(Ala or -continued Pro)Lys(Arg or Ala)Val(His)Ala(Val)Arg(Thr or Lys)
(160)
Thr(Gln or His)LeuPro wherein each of the amino acid residues, X, Y or Z shown in parentheses may individually replace the contiguous amino acid residue to the immediate left of the parentheses, X and/or Y and/or Z in the peptide amino acid residue sequence independently denote the absence of an amino acid residue in the position of the contiguous amino acid residue to the immediate left of the parentheses whereby the peptide length is shortened by one, two, or three amino acid residues, respectively, and the parenthesized numerals above particular amino acid residues in the above sequence illustrate positions of the particular amino acid residue relative to the amino-terminus of the $VP_1$ capsid protein of Tübingen type O, subtype 1, strain Kaufbeuren FMDV. Those numerals are presented for reference purposes.

The more particularly preferred foot-and-mouth disease-related peptide amino acid sequence corresponding to positions of about 141 to about 160 from the amino-terminus commences at the amino-terminus with the Val(Ser or Gln or X) residue at position 141 in the above sequence.

Most particularly preferred, individual peptides are those corresponding substantially to amino acid residue sequences of foot-and-mouth disease viruses (1) Tübingen type O, subtype 1, strain Kaufbeuren, (2) type A, subtype 10, strain 61 and (3) type A, subtype 12, strain 119 at the positions of about 141 to about 160, taken from left to right as shown and in the direction from amino-terminus to carboxy-terminus, and are selected from the following respective sequences:

(1) ValProAsnLeuArgGlyAspLeuGlnVal-LeuAlaGln LysValAlaArgThrLeuPro;

(2) SerArgSerGlyAspLeuGlySerIleAlaAlaArg ValAlaThrGlnLeuPro, and (3) SerGlyValArgGlyAspPheGlySerLeuAlaProArg ValAlaArgLeuPro.

The particularly prefered sequence of about twenty amino acid residues of the polio $VP_1$ capsid-related synthetic peptides corresponds to the $VP_1$ capsid in the amino acid residue positions regions of about 61 to about 80 and about 181 to about 201 from the amino-terminus. The amino acid residues of these sequences, written from left to right and in the direction from amino-terminus to carboxy-terminus, are respectively shown below:

carboxy-terminus, are respectively shown below:
(61)
ValGlnThrArgHisValValGlnHis(Arg)ArgSerArgSer
(80)
GluSerSer(Thr)IleGluSerPhe; and
(181)
SerIlePheTyrThrTyrGlyThr(Ala)AlaProAlaArgIle
(201)
SerValProTyrValGlyIle wherein each parenthesized amino acid residue in each sequence may independently replace the contiguous amino acid residue to the immediate left of the parentheses, and the parenthesized numerals above particular amino acid residues in the above sequence illustrate positions of the particular amino acid residue relative to the amino-terminus of the $VP_1$ capsid protein of polio type 1 virus. These numerals are presented for reference purposes.

The present invention provides several benefits and advantages, particularly in the case of the use of peptides of this invention in vaccines against Picornavirus-induced diseases and in diagnostics for assaying for the presence of these diseases or viruses in animals, including man.

Thus, one salient advantage is that the synthetic peptides can provide part of a vaccine that protects animals from these diseases.

A particular benefit of the invention is that vaccines prepared using a synthetic peptide do not have to be refrigerated prior to administration in order to obtain efficacious vaccinations.

Another advantage of the present invention is in the realm of diagnostics wherein antibodies in antisera raised to the synthetic peptide immunoreact with and can be used to detect the presence of antigenic proteins and antibodies associated with Picornaviruses such as foot-and-mouth disease and polio.

Still further benefits and advantages will be apparent to those skilled in the art from the detailed description, Examples and claims that follow.

BRIEF DESCRIPTION OF THE DRAWINGS

In the drawings forming a portion of this disclosure:

FIG. 1 shows eight amino acid residue sequences at amino acid residue positions 130–160 of the $VP_1$ capsid from foot-and-mouth disease viruses, using the usual three letter code for each amino acid residue. The sequences are read from left to right and in the direction from amino-terminus toward carboxy terminus. The numerals 130, 140, 150 and 160 represent amino acid residue positions relative to the amino-terminus of Tübingen type O, subtype 1, strain Kaufbeuren virus, (Olk), with the amino acid residue sequences of the remaining virus $VP_1$ capsids adjusted by the inclusion of one or more hyphens so that the homologies between those sequences are more apparent. The abbreviations for viruses in addition to Olk are as follows:

Olc=type O, subtype 1, strain Campos; A10=type A, subtype 10, strain 61; A12=Type A, subtype 12, strain 119, A24=type A, subtype 24; A27=type A, subtype 27; A79=type A, subtype 79; and C3=type C, subtype 3, strain Indaial.

FIG. 2 shows amino acid residue sequences at amino acid residue positions 61–80 and 182–201 of the $VP_1$ capsid from polio type 1 Mahoney and Sabin viral strains and from the type 3 Leon polio virus strain, using the usual three letter code for each amino acid residue. The sequences are read from left to right in the direction from amino-terminus toward carboxy-terminus. The numerals 61, 80, 182 and 201 represent amino acid residue positions relative to the amino-terminus of the Mahoney type 1 polio virus $VP_1$ capsid protein.

DETAILED DESCRIPTION OF THE INVENTION

I. General Discussion

The present invention comprises the discovery that a particular, comparatively short, synthetic peptide sequence is, most unexpectedly and most suprisingly, extremely active antigenically. The synthetic, peptide contains an amino acid residue sequence about 20 acids in length. The peptide's amino acid resudue sequence at least corresponds to an amino acid residue sequence of a region on the antigenic Picornavirus capsid protein that is located at a distance equal to about 60 to about 75 percent of the total amino acid residue sequence length the antigenic capsid protein as measured from the amino-terminus thereof. The synthetic peptide contains a net zero to positive ionic charge, exclusive of ionic charges present due to the presence of terminal amino and/or carboxyl groups.

In addition, synthetic antigens including the peptide sequences described hereinafter are mono-specific to the specific serotypes, subtypes and strains of Picornaviruses such as the foot-and-mouth disease virus, and are also poly-specific, albeit to a lesser extent, to a plurality of the serotypes, subtypes and strains of viruses.

Synthetic, peptides related to the Picornavirus that causes foot-and-mouth disease (FMD), vaccines and diagnostics utilizing such peptides will be discussed as exemplary synthetic peptides, vaccines and diagnostics that can be prepared. It is to be understood, however that the general principles, techniques and definitions disclosed herein for FMDV are also applicable to synthetic peptides related to other genera of the Picornavirus family. Specific amino acid sequences corresponding to amino acid residue positions of the FMDV VP$_1$ capsid relate only to that virus, however, as do specific amino acid residue sequences corresponding to the amino acid residue positions of polio VP$_1$ capsid.

In particular, it has been discovered, that a synthetic peptide containing about twenty amino acids corresponding to the amino acid residue sequence of postions about 130 to about 160, and positions about 141 to about 160 especially, from the amino-terminus of the FMDV VP$_1$ protein such as that from Tübingen type O, subtype 1, strain Kaufbeuren has much higher antigenic efficacy and activity than ever had been suggested or predicted from earlier studies. A peptide of this invention, alone, in straight chain or cyclic ring form, as a polymer having peptide units linked by oxidized cysteine residues of adjacent peptides, or as a conjugate linked to a carrier, is a potent immunologic reactor (antigen) for foot-and-mouth disease, as will be discussed in detail hereinafter.

The phrases "about position 130 to about position 160" and "about position 141 to about position 160" from the amino-terminus and similar phrases are used herein. Those amino acid residue postions are determined in relation to the reference VP$_1$ capsid protein of type O, subtype 1, strain Kaufbeuren FMDV.

It is noted that some workers in this field such as Kleid et al. in EPO publication number 0 068 693 A2 have offset the positions of amino acid residues in the 130-160 region of the VP$_1$ (VP$_3$, discussed hereinbefore) capsid protein by one amino acid position number toward the carboxy-terminus relative to the position numbers given herein due to the presence of an additional amino acid (Val) after Asp-53 in the sequence of the type C, subtype 3 VP$_1$ capsid, where the other capsids contain no amino acid residue. Consequently, the amino acid at a given position such as 140 herein appears as the amino acid at position 141 in the above-mentioned EPO application. Thus, there is an art-recognized difference of one or more amino acid positions when different workers report sequences of the same protein molecule.

In addition, capsid proteins from some foot-and-mouth disease viruses contain no amino acid residue at one or more positions the 130-160 region relative to type VP$_1$ of type O, subtype 1, strain Kaufbeuren as is shown in FIG. 1 and designated by the letters "X", "Y" and "Z" in the sequence of Formula I, hereinbelow. In view of the presence of such deletions or omissions, some workers report amino acid positions as determined from the protein or a DNA molecule coding for that protein, without accounting for the deletions. Other workers illustrate the homologies between the VP$_1$ capsids by indicating amino acid deletions with hyphens, letters or other indicia and numbering the remaining amino acid residue positions as if the deleted residues were present, as is done herein. Thus, there is an additional, slight, art-recognized variation in the reporting of amino acid positions.

Thus, the word "about" as used in the above and similar expressions is meant to indicate that the amino acid residue sequence may start or end at an amino acid residue up to three residues on either side of the named positions to allow for the variation of one to two position numbers as reported in the art for a given amino acid residue in any particular, peptide sequence, and also to take into account the fact that certain amino acid residues are omitted in some VP$_1$ capsid proteins.

Several synthetic peptides are contemplated by this invention. Each of these synthetic peptides contains a sequence including about 20 amino acid residues in a sequence that corresponds or corresponds substantially to an amino acid residue sequence of about the same length in the region from about position 130 to about position 160 of the VP$_1$ protein of FMDV.

As has already been noted, there are several types, subtypes and strains of FMDV. Therefore, for convenience of reference, the peptide sequences described herein will be discussed with reference to the VP$_1$ protein from a particular type, subtype and strain; namely Tübingen type O, subtype 1, strain Kaufbeuren of FMDV, also referred to herein as type O, subtype 1, strain Kaufbeuren and Olk. Thus, using the amino acid sequence of one particular FMDV protein as a reference, other useful peptide sequences are described which contain substituted or omitted amino acid residues at particular locations along the peptide chain.

Peptide sequences from the VP$_1$ capsid protein of eight of FMD viruses at postions of about 130 to about 160 are shown in FIG. 1, using the numbering system of the reference type Olk protein. Synthetic, preferably water-soluble, peptides each containing about 20 amino acids, having amino acid residue sequences that correspond or correspond substantially to the amino acid residue sequences shown in FIG. 1 and meeting the unitary test condition hereinafter are contemplated as being within the scope of this invention.

A preferred peptide having an amino acid residue sequence that corresponds to amino acid residue positions of about 130 to about 160, taken from left to right and in the direction from amino-terminus to carboxy-terminus is shown in Formula I, below;

---

Formula I (130)
TyrAsn(Asp or Thr)Gly(Phe)Glu(Thr)Cys(Ser or Asn or Thr)Arg(Lys or Thr)TyrAsn(Ala or Ser or Thr)Arg(Val or Ala or Asn or Thr)Asn(Gly or Ser)
(140)
Ala(Asp or Gly)Val(Ser or Gln or X)Pro(Gly or -continued Formula I Y)Asn(Z)Leu(Arg or Val)Arg(Ser or Ala)GlyAspLeu(Met
or Phe)Gln(Gly)
(150)
Val(Thr or Ser or His)Leu(Ile)AlaGln(Ala or
Pro)Lys(Arg or Ala)Val(His)Ala(Val)Arg(Thr or Lys)
160
Thr(Gln or His)LeuPro wherein each of amino acid residues, X, Y or Z in parentheses may independently replace the contiguous amino acid residue to the immediate left of the parentheses; i.e., the amino acid residue closer to the amino-terminus;

X and/or Y and/or Z in the peptide amino acid residue sequence independently denote the absence of an amino acid residue in the position of the contiguous amino acid residue to the immediate left of the parentheses (closer to the amino-terminus) whereby the peptide length is shortened by one, two or three amino acid residues, respectively, and the parenthesized numerals above the above particular amino acid residues in the sequence illustrate positions of the particular amino acid residue from the amino-terminus of the $VP_1$ capsid protein of Tübingen type O, subtype 1, strain Kaufbeuren FMDV. The numerals are presented for reference purposes.

The more preferred sequence corresponding to positions of about 141 to about 160 of the $VP_1$ capsid protein commences at the amino-terminus with the Val(Ser or Gln or X) residue at position 141 in Formula I.

Poly-specificity and cross-reactivity among types, subtypes and strains of the FMDV genus are improved by use of an antigenic peptide of this invention whose amino acid residue sequence corresponds to an amino acid residue sequence of at least more than one strain, and more preferably more than one subtype or serotype of the FMDV genus. The amino acid residue sequence of such a peptide may not correspond substantially to the amino acid residue sequence of any one virus, but may nevertheless, when inoculated as a vaccine into an animal host, induce production of antibodies that immunoreact with a plurality of virus types, subtypes or strains and protect the host from more than one of those viruses.

A poly-specific peptide whose amino acid residue sequence corresponds to an amino acid residue sequence of at least more than one strain of FMDU may have the amino acid residue sequence of Formula 1, above, in which one or more parenthesized amino acid residue, X, Y, or Z replaces the contiguous amino acid residue to the immediate left of the parentheses; i.e. the contiguous amino acid residue toward the amino-terminus. Substitutions and omissions in the region of amino acid residue positions about 141 to about 155 are preferred for obtaining poly-specificity in a peptide having a single amino acid residue sequence. Such a poly-specific peptide can be prepared and used in the same way as any other peptide of this invention.

Most particularly preferred, individual peptides corresponding substantially to amino acid residue sequences of (1) Tübingen type O, subtype 1, strain Kaufbeuren, (2) type A, subtype 10, strain 61 and (3) type A, subtype 12, strain 119 at the positions of about 141 to about 160, taken from left to right in the direction from amino-terminus to carboxy-terminus, are represented by the following respective sequences:

(1) ValProAsnLeuArgGlyAspLeuGlnVal-LeuAlaGln LysValAlaArgThrLeuPro;

(2) SerArgSerGlyAspLeuGlySerIleAlaAlaArg ValAlaThrGlnLeuPro, and (3) SerGlyValArgGlyAspPheGlySerLeuAlaProArg ValAlaArgLeuPro.

The term "corresponds substantially" in its various grammatical forms is used herein and in the claims in relation to peptide sequences related to Picornaviruses to mean the peptide sequence described plus or minus up to three amino acid residues at either or both of the amino- and carboxy-termini and containing only conservative substitutions in particular amino acid residues along the peptide sequence. The term "corresponds" in its various grammatical forms is used herein and in the claims in relation to peptide sequences related to Picornaviruses to mean the peptide sequence described plus or minus up to three amino acid residues at either or both of the amino- and carboxy-termini and containing conservative as well as radical substitutions in particular amino acid residues and also containing deletions or additions of particular amino acid residues along the peptide sequence.

The term "conservative substitution" as used above is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like.

In some instances, the replacement of an ionic residue by an oppositely charged ionic residue such as Asp by Lys has been termed conservative in the art in that those ionic groups are thought to merely provide solubility assistance. In general, however, since the replacements discussed herein are on relatively short synthetic peptide antigens, as compared to a whole protein, replacement of an ionic residue by another ionic residue of opposite charge is considered herein to be "radical replacement", as are replacements between nonionic and ionic residues, and bulky residues such as Phe, Tyr or Trp and less bulky residues such as Gly, Ile and Val.

The terms "nonionic" and "ionic" residues are used herein in their usual sense to mean those amino acid residues that normally either bear no charge or normally bear a charge, respectively, at physiological pH values. Exemplary nonionic residues include Thr and Gln, while exemplary ionic residues include Arg and Asp.

The above sequence shown in Formula 1 and the shorter, more preferred synthetic sequence corresponding to positions about 141 to about 160 of the FMDV $VP_1$ capsid include a large number of individual peptides, each of which, when about 20 amino acid residues in length, is a peptide of this invention. For example, synthetic peptides prepared having an amino-terminus beginning at position 141 of the capsid may start with an amino-terminal Val, Ser or Gln residue.

In addition, when the amino-terminal amino acid residue position is represented by X, indicating the absence of the amino acid residue to the immediate left of the parentheses in Formula I, the peptide amino-terminus may begin with the amino acid residues Pro, Gly or Y of capsid position 142, wherein Y independently denotes the absence of Pro and Gly so that the peptide amino-terminus begins with the amino acid residue corresponding to position 143 of Olk, rather than the positions 141 or 142. Further examination of Formula 1 illustrates that the residue of capsid position 143 can be Asn or Z and thereby also be absent.

Thus, a peptide whose sequence corresponds to capsid positions about 141 to about 160 could begin at capsid position 144. As pointed out before, peptide sequences that correspond to a described sequence may have plus or minus up to three amino-terminus residues at either terminus. The above-described peptide whose amino acid residue sequence actually begins at position 144 relative to the type Olk $VP_1$ capsid protein is among those whose sequences are "minus up to three amino acid residues at either or both of the amino- and carboxy-termini . . ."

Exemplary peptides which are encompassed in the present invention are included in the about 130 to about 160 region of type O, subtype 1, strain Kaufbeuren and type A, subtype 12, strain 119 FMDV proteins (expressed using the type O position numbering and denominated Olk and A12, respectively), and the corresponding regions of type C, SAT-1, SAT-2, SAT-3 and ASIA-1. Two examples of such peptides are shown below using Olk virus positional numbering, and a hyphen to indicate an omitted amino acid residue.

| Example 1 |
| --- |
| Type Olk |
| (130) (140) |
| TyrAsnGlyGluCysArgTyrAsnArgAsnAlaValProAsnLeuArg |
| (150) (160) |
| GlyAspLeuGlnValLeuAlaGlnLysValAlaArgThrLeuPro |
| Type A12 |
| (130) (140) |
| TyrAsnGlyThrAsnLysTyrSerAlaSerGlySerGly - ValArgGlyAsp |
| 150 161 |
| PheGlySerLeuAlaProArgValAlaArgGlnLeuProAla |

It has also been established that the amino acid residue sequence of capsid region about 141 to about 160 is uniquely and highly unexpectedly antigenically active and potent, as discussed in greater detail hereinafter.

Peptides having a sequence of approximately twenty amino acids, within the about 130 to about 160 region, and in the about 141 to about 160 region in particular, to which an amino- or carboxy-terminal Cys or other amino acid may be added to permit attachment by covalent linking by an additional synthesis step to a carrier, e.g. keyhole limpet hemocyanin (KLH), if a carrier is to be used, are one embodiment of invention, as are the above peptides with variations in peptide length or substitutions or deletions as to individual amino acids which do not destroy or substantially alter the unique and potent antigenicity exhibited by the FMDV monospecific and polyspecific synthetic antigenic determinant peptides of this invention.

These sequences, separated from other antigenically active or antigenically masking sequences, constitute an embodiment of this invention in yet another form. Antigens comprising more than one of the foregoing antigenically active sequences, separate from antigenically interfering or masking sequences, chemically associated or mixed with each other constitute still another form of the invention. Antigens comprising a carrier to which one or more of the foregoing antigenically active amino acid sequences is attached constitutes a further embodiment of this invention. The present invention, of course, also embodies a vaccine containing an antigenic peptide of this invention alone or linked to a carrier along with a physiologically tolerable diluent. The presence of physiologically tolerable diluting adjuvants is optional.

In considering the present invention it is important to recognize the following definition of the antigenically active amino acid residue sequences which are considered as one embodiment of the invention. For example, the sequence corresponding to positions 141 to 160 of type O, subtype 1, strain Kaufburen taken from left to right in the direction from amino- to carboxy-terminus
ValProAsnLeuArgGlyAspLeuGlnValLeuAlaGlnLys-
Val AlaArgThrLeuPro when separated from other peptides, gene fragments, amino acids and amino acid sequences which tend to mask or to interfere with or to cross-react or complicate the antigenic effectiveness of the subject peptide is a specific embodiment of the subject invention. Thus, while one may find the specified sequence as part of a large protein or a larger peptide containing, e.g., about 30 amino acids or more, such larger materials do not constitute the present invention because a protein or a larger peptide would not possess the activity, the unusually and unexpectedly high level of substantially monospecific antigenic activity, possessed by an about 20 amino acid long peptide of this invention.

The term, "FMDV mono-specific synthetic antigenic determinant peptide" means the particular peptide specified as described above resulting from a chemical synthesis which eliminates the possibility of fragments of genes, proteins or peptides, or any amino acid compounds orignating directly or indirectly from FMDV and free of peptide or amino acid sequences which would interfere with or alter the monospecific antigenic activity of the specified peptide in inducing antibody production to FMDV in animals. It is noted that although the term "monospecific" is used herein, the individual peptides also exhibit poly-specific antigenic activity with a plurality of FMDV types, subtypes and strains. This broadened specificity is particularly found where a radical substitution is made in a peptide whose sequence otherwise corresponds substantially to an amino acid residue sequence of a particular FMDV capsid and the radically substituted amino acid residue is a residue found at the position of substitution in another viral strain. Thus, use of the term "mono-specific" is a shorthand description for the broader specificity of the peptides of this invention.

The synthetic, antigenic peptides of this invention alone in straight chain or cyclic ring form, as a polymer wherein adjacent peptide repeating units are bonded together by oxidized cysteine residues, or as a conjugate linked to a carrier when introduced in an effective amount as a vaccine into an animal host are typically capable of inducing production of antibodies in the host that immunoreact with the related Picornavirus and protect the host from infection caused by that Piconavirus. However, a peptide of this invention can be further defined by a unitary test of its antigenic characteristics that is independent of the form in which the peptide is ultimately used; i.e. in straight chain, cyclic ring, polymeric or linked as a conjugate. According to this unitary test, a peptide of this invention in straight chain form when linked to a keyhole limpet hemocyanin carrier as a conjugate and introduced in an effective amount as a vaccine into a host animal is capable of inducing production of antibodies that immunoreact with its related Picornavirus and protect that host from that virus. The amounts of peptide and carrier, and the specific reaction conditions for the conjugation reaction and vaccine preparation are given in Bittle et al., *Nature*, 298:30-33 (July, 1982).

As a vaccine, the present invention comprises an effective amount of a peptide antigen which may, alone, serve as the vaccine when present with a physiologically acceptable diluent such as water or saline. The vaccine may include a carrier, which may be of any of numerous carriers such as keyhole limpet hemocyanin (KLH), tetanus toxoid, poly-L-(Lys:Glu), peanut agglutinin, ovalbumin, soybean agglutinin, bovine serum albumin (BSA) and the like, to which a FMDV monospecific synthetic antigenic determinant peptide is linked. A polymer prepared by linking a plurality of peptides of this invention as through end-to-end linking of oxidized terminal cysteine groups may also comprise an exogenous carrier-free vaccine along with a physiologically acceptable diluent. In each instance, the peptide of this invention functions as the specific antigenic determinant.

The "effective amount" of antigenic peptide depends upon a number of factors Included among those factors are the body weight and species of animal host to be protected, the carrier when used, the adjuvant when used, the number of inoculations desired to be used, and the duration of protection desired for the animal. Individual inoculations typically contain about 20 micrograms of synthetic antigenic peptide to about 2 milligrams, exclusive of any carrier to which the peptide may be linked.

When the antigenic vaccine of this invention is introduced into the desired host, it initiates the production of antibodies in the host to the aforesaid antigenic peptide and to the related Picornavirus such as FMDV. Vaccines containing effective amounts of the peptides of this invention not only initiate production of antibodies in the host, but those antibodies are produced in a sufficient amount to protect the animal host from infection with FMDV or another Picornavirus. Protection of the host can be assessed by the level of neutralizing antibody raised and/or the neutralizing index, discussed further hereinbelow.

The invention also contemplates antigens in which all or part of the entire carrier is antigenic. Thus, a separate carrier portion may or may not be used. The synthetic antigen formed by linking the FMDV mono-specific snythetic antigenic determinant peptide to an antigen carrier as well as the methods of preparing such synthetic antigens are specific aspects of the present invention.

In general, the synthetic antigen may be formed by the steps of preparing the Picornavirus-related peptide such as a FMDV mono-specific synthetic antigenic determinant peptide, which immunologically corresponds or corresponds substantially to antigenic determinants of FMDV, and coupling the synthetic determinant to a pharmaceutically acceptable carrier in a separate synthetic step.

As a method of manufacturing vaccines, the method comprises synthesizing FMDV mono-specific synthetic antigenic determinant peptide which antigenically is the duplicate or substantial duplicate of specified determinant portion of the FMDV VP$_1$ protein. The synthetic peptide may be, but need not always be, linked to a carrier, to result in an antigen in which the antigenicity is that of the FMDV mono-specific antigenic determinant peptide and which, when introduced into a host along with a physiologically tolerable diluent, initiates production of antibodies to the FMD virus.

As a method of manufacturing antibodies, the vaccine as described above is injected into a host and antibodies raised in the host to the protein antigen are harvested from host fluids for use in conventional diagnostic procedures to detect the presence of the protein antibody or as therapeutic agents for passive immunoprophylaxis.

It will be understood that while there are many procedural steps utilizing many materials in the manufacture of the vaccines and antibody preparations of this invention, as discussed in detail hereinafter, the invention is not limited to the utilization of any particular steps or reagents or conditions, but rather the invention is conceptually as stated above and as defined with particularity in the claims append hereto.

I. Peptide Synthesis

Peptides discussed hereinafter were synthesized using known procedures. [See, e.g., Marglin, A. and Merrifield, R.B., *Ann.Rev. Biochem.*, 39:841-866 (1970).] The peptides were coupled to the protein carrier KLH through a cysteine residue which was typically added at the carboxy-terminus of the peptide unless otherwise noted. The synthetic linking step of peptide to the protein carrier, unless otherwise specified, was carried out by addition of the cysteine sulfur atom to the double bond of the reaction product between the carrier and N-maleimidobenzoyl-N-hydroxy succinimide ester (MBS), following the general procedure described by Lieu et al, *Biochemistry*, 18:690-697 (1979).

A low molecular weight, presumably cyclic peptide was prepared by synthesising a peptide having the amino acid sequence of the Olk VP$_1$ at positions 141-160 (FIG. 1) and adding cysteine (Cys) residues at both the amino- and carboxy-termini (diCys peptide). Thereafter, 10 milligrams of the diCys peptide (containing Cys residues in un-oxidized form) were dissolved in 250 milliliters of 0.1 molar ammonium bicarbonate buffer in a beaker. The dissolved diCys peptide was then air oxidized by stirring the resulting solution gently over a period of about 18 hours. At the end of that time period, an Ellman reaction indicated the presence of no free mercaptan. [Ellman, *Arch. Biochem. Biophys.*, 82:70-77 (1959).]

The obtained solution was freeze dried. The dried material so produced and hereinafter referred to as the cyclic peptide, or cyclic ring peptide has the amino acid sequence noted before for positions 141-160 of the Olk VP$_1$ capsid believed to be bonded together amino-terminus to carboxy-terminus by oxidized cysteine residues; i.e., by one cystine residue containing a disulfide bond. Two or more diCys peptides may also be linked together to form the cyclic ring peptide.

Two polymeric peptides were also prepared from the above peptide containing un-oxidized Cys residues at both peptide termini (diCys peptide) and bonded to those termini by peptide amide linkages. These polymeric peptides are referred to hereinafter as polymeric peptides A and B.

Polymeric peptide A was prepared from the diCys peptide by dissolving that peptide at a concentration of 5 milligrams per milliliter in the above ammonium bicarbonate buffer. Air oxidation as above produced a material that had no free mercaptan by the Ellman reaction. The reaction solution contained no particulate matter after oxidation and was freeze dried to obtain polymeric peptide A in dry form.

Polymeric peptide B was prepared in the same buffer with the same oxidizing conditions as polymeric peptide A and the cyclic peptide. Here, however, the concentration of diCys peptide used during oxidation was 23 4 milligrams per 1.2 milliliters of buffer. No free mercaptan was noted by the Ellman reaction after the oxidation reaction, but a small amount of precipitate present in the reaction mixture was observed. The reaction mixture was freeze dried to recover polymeric peptide B, including the precipitate.

Each of the above prepared dried solids (cyclic peptide and polymeric peptides A and B) was used without further purification. Vaccines were prepared from those dried solids by suspending them in complete Freund's adjuvant at concentrations sufficient to provide 100 micrograms of peptide per inoculation.

III. Immunizations

A. Inoculations

The vaccines used herein contain the stated amount of peptide alone, in straight chain or cyclic form, as a polymer of individual peptides linked through oxidized cysteine residues (cystine) or linked to a carrier. The stated amounts of peptides refer to the weight of peptide without the weight of a carrier, when a carrier was used.

The vaccines also contained a physiologically tolerable diluent such as water or saline, and further typically included an adjuvant. Complete Freund's adjuvant (CFA) and incomplete Freund's adjuvant (IFA) are materials well known in the art and are available commercially from several sources. Saponin, a plant-produced glycoside, is also a well known adjuvant available commercially from Berghausen Chemical Company, Cincinnati, Ohio as a 5 percent solids solution, and was used herein along with aluminum hydroxide.

Vaccine stock solutions were prepared with IFA or CFA as follows: An amount of the synthetic peptide, polymeric peptide or conjugate sufficient to provide the desired amount of peptide per inoculation was dissolved in phosphate buffered saline (PBS). Equal volumes of CFA or IFA were then mixed with the peptide solution to provide a vaccine containing peptide, water and adjuvant in which the water-to-oil ratio was 1:1. The mixture was thereafter homogenized to provide the vaccine stock solution.

Vaccine stock solutions were prepared with saponin-aluminum hydroxide as follows: Aluminum hydroxide in an amount of 10 milligrams per milliliter was suspended in an aqueous 0.85 percent solution of sodium chloride. An amount of the synthetic peptide, polymeric peptide or conjugate sufficient to provide the desired peptide amount per inoculation after a dilution to 20 percent was admixed with the aluminum hydroxide suspension and allowed to sorb onto the aluminum hydroxide particles for 2–3 hours. One part of the suspension so prepared was then diluted with 4 parts of a previously diluted saponin solution to form the stock solution of vaccine in which the saponin was present at 0.125 weight percent.

Preliminary, screening assays were by enzyme-linked immunosorbent assay (ELISA) as discussed by Bittle et al., *Nature,* 298:30–33 (July, 1982), incorported herein by reference, in which peptide-antipeptide antibody immunoreactions were measured. Viral neutralization index measurements which measure viral inactivation by immunoreactions between induced antibodies and live virus particles, were also conducted as described by Bittle et al. Further specifics for the techniques utilized and the results obtained herein and related to work with FMDV may be found in Bittle et al.

B. Antibodies To Peptides Homologous To Particular FMD Viruses

Responses to various peptide regions of the $VP_1$ or FMDV type O, subtype 1, strain Kaufbeuren are given in Table 1. These data summarize antibody responses in rabbits, using conventional protocols and illustrate neutralization of a FMD virus containing an amino acid sequence homologous to that of the peptide used for immunization. (For details of exemplary protocols, see Lerner et al. U.S. patent application Ser. No. 248,059 filed Mar. 27, 1981, and Bittle et al., supra.)

TABLE 1

ANTIBODY RESPONSE TO DIFFERENT PEPTIDES IN INDIVIDUAL RABBITS

| KLH-Peptide Antigen[1] | Neutralization Index[2], ($log_{10}$) |
|---|---|
| 9–24 | ≦0.3 |
| 9–24 | ≦0.3 |
| 17–32 | ≦0.5 |
| 17–32 | ≦0.9 |
| 25–41 | ≦0.5 |
| 25–41 | ≦0.9 |
| 1–41 | ≦0.9 |
| 1–41 | ≦0.7 |
| 141–160 | ≦3.9 |
| 141–160 | ≦3.7 |
| 151–160 | 2.9 |
| 151–160 | 1.1 |
| 200–213 | 3.5 |
| 200–213 | 3.1 |

[1]The numbers refer to the amino acid residue position, starting at the amino-terminus of the O1k $VP_1$ capsid to which the amino acid residue sequences of the synthetic peptides substantially corresponded.

[2]Specific details for the procedures used to obtain these data are found in Bittle et al., supra.

It is emphasized that the neutralization indices for the peptides having the amino acid residue sequence of the 141–160 region in Table 1 were each greater than 3.9 and 3.7, respectively, while the indices shown for the 200–213 region peptides were found to be 3.5 and 3.5, respectively. Synthetic peptides having amino acid residue sequences corresponding substantially to the designated 141–160 and 200–213 amino acid residue positions both neutralized the viruses. However, the neutralization indices of the peptides of this invention whose sequences corresponded substantially to the sequence of amino acid residue positions 141–160 were actually greater than the indices shown. The magnitude of the real difference in neutralization index is shown in Table 4, hereinafter, for another comparison of the same peptides inoculated into rabbits wherein more sensitive neutralization end point determinations were made.

It was established that a single innoculation of the antigens was effective in producing neutralizing antibodies in animals and in protecting them against challenge. Table 2 summarizes these results, on guinea pigs, carried out using standard protocol (see Lerner et al patent application and Bittle et al., supra) Table 2 shows the efficacy of the antigens and, also, shows the markedly surprising antigenicity of the 141–160 region of the $VP_1$ protein. A neutralizing index of about 1.5 or greater indicates that the animal was protected against the virus.

TABLE 2

PROTECTION OF GUINEA PIGS AGAINST CHALLENGE WITH FOOT-AND-MOUTH DISEASE VIRUS BY INNOCULATION SYNTHETIC PEPTIDES

| KLH-Peptide Antigen[1] | Dose (Micrograms) | Adjuvant | Neutralization Index[2], ($\log_{10}$) | Protection[3] |
|---|---|---|---|---|
| 141–160 | 20 | Al(OH)$_3$ | 2.1 | 3/3 |
|  | 200 | Al(OH)$_3$ | 2.7 | 3/3 |
|  | 20 | Freund's[4] | 2.1 | 3/3 |
|  | 200 | Freund's[4] | ≧3.3 | 4/4 |
| 200–213 | 20 | Al(OH)$_3$ | 1.1 | 1/3 |
|  | 200 | Al(OH)$_3$ | 0.7 | 2/4 |
|  | 20 | Freund's[4] | 1.1 | 0/4 |
|  | 200 | Freund's[4] | 0.5 | 0/4 |

[1] See Table 1, Footnote 1.
[2] Neutralizing activity of pooled serum from eight animals. See Bittle et al., supra.
[3] Number of animals protected/number of animals challenged.
[4] Complete Freund's adjuvant.

The above data show that the particularly preferred peptide having the amino acid sequence of amino acid residue positions 141 to 160 of the Olk VP$_1$ capsid includes amino acid residues on either side of the peptide of positions 146–154 predicted by Strohmaier et al., supra, to possess antigenic activity for that capsid protein. In addition, the peptide having the Olk sequence at positions 141–160 contains amino acid residue sequences (141–145 and 155–160) predicted by Stromaier et al, supra, to be inactive, non-inducing peptides.

The results in Tables 1 and 2, above, illustrate that Stromaier et al. were incorrect in their prediction as to where in the amino acid residue sequence neutralizing antibodies would and would not be raised. The results in Table 3 below, wherein the particularly preferred peptide of this invention having the amino acid residue sequence of positions 141–160 of Olk VP$_1$ is compared to the peptide of Stromeier et al. having the sequence of positions 146–155 of Olk VP$_1$, show that the peptide of this invention is about 1000 to about 100,000 times more active in producing neutralizing antibodies than is the predicted peptide of Stromaier et al. An averaged value of those results also indicates that the Stromaier et al. peptide does not induce production of sufficient amounts of antibodies to provide protection to the animal host (neutralization indices of 1.1 and 1.5) while the peptide of this invention provides large amounts of protective antibodies (neutralization indices equal to or greater than 4.3 and 2.7).

TABLE 3

ANTIBODY RESPONSES TO DIFFERENT PEPTIDES IN INDIVIDUAL RABBITS[1]

| KLH-Peptide Antigen[2] | Viral Serotype[3] | Neutralization Index, ($\log_{10}$) Rabbit #1 | Rabbit #2 |
|---|---|---|---|
| 141–160 | O | >4.3 | 2.7 |
| C141–160[4] | O | 3.3 | >4.3 |
| 141–160 | A[5] | 1.3 | 2.9 |
| 146–155[6] | O | 1.1 | 1.5 |
| 130–161 | O | <1.0 | <1.0 |

[1] Antibody response and virus neutralization protocols were carried out as described for Table 1.
[2] See Table 1, Footnote 1.
[3] Viral serotype whose amino acid residue sequence was utilized for preparation of the antigenic peptide and the virus against which neutralization was determined.
[4] The carrier-linking Cys residue was placed at the amino-terminus rather than carboxy-terminus as was the case for the other peptides.
[5] Serotype A, subtype 10, strain 61 FMDV.
[6] Amino acid residue region predicted as active by Stromaier et al., supra.

The data in the above Table also illustrate that the 32 amino acid peptide having the sequence of positions 130–161 of Olk VP$_1$ is inactive in producing neutralizing antibodies. The data-relating to the KLH-peptide antigen denominated C141–160 show that neutralizing antibody production is not a function of which terminus of the peptide is linked to the carrier.

C. Cross-Reactivity of Antigenic Peptides With Heterologous FMD Viruses

The antigenic peptides of this invention are mono-specific, as previously defined. However, these peptides also have varying amounts of cross-reactivities with viral serotypes whose amino acid sequences are heterologous to the specific amino acid sequence of a given peptide. Thus, the peptides are also poly-specific, to varying degrees.

The data of Table 4, below, illustrate the cross-reactivity of antibodies raised to antigenic peptide conjugates having the sequence of amino acid positions 141–160 and 200–213, respectively, of Olk VP$_1$ used to immunize two rabbits for each sequence. Neutralization indices were determined against the homologous virus (Olk) and the heterologous types A and C viruses. Those data show that serotype specificity of sera produced by inoculation of the synthetic antigenic peptide mimics that found with sera against the whole virus. The cross-neutralization is thought to reflect the sequence homology among different serotypes, as is shown in FIG. 1.

TABLE 4

SEROTYPE SPECIFICITY OF THE RABBIT ANTI-PEPTIDE ANTIBODIES

| Antisera to Peptide Region | Neutralization Index, ($\log_{10}$) Against FMD Viruses[1] | | |
|---|---|---|---|
|  | O1k[2] | C3[3] | A10[4] |
| 141–160 | 4.3 | −0.1 | 1.1 |
| 141–160 | ≧6.3 | 1.9 | 2.3 |
| 200–213 | 2.9 | −0.1 | 1.5 |
| 200–213 | 3.3 | 0.3 | 1.5 |

[1] Virus neutralization protocols are as described for Table 1.
[2] Tubingen type O, subtype 1, strain Kaufbueren.
[3] Type C, subtype 3, strain Indaial.
[4] Type A, subtype 10, strain 61.

Table 4 also shows the great difference in neutralizing index against Olk between the synthetic peptides whose amino acid residue sequences correspond substantially to positions 141–160 and 200–213, respectively, of Olk. Thus, in the data shown above, the peptide, also predicted as immunologically active by Strohmaier et al., supra, whose amino acid residue sequence corresponds substantially to positions 200–213 of Olk provided neutralization index values similar to those shown in Table 1 for the same peptide under similar conditions. However, the neutralization indices observed for the peptide of this invention whose amino acid residue sequence corresponded substantially to positions 141–160 of Olk were about one to about three units higher, corresponding to an improvement in neutralization of about 10 to about 1000 fold.

D. Antibodies From Cystine-Linked Peptides

Stock solutions of vaccines containing the three cystine-linked peptides (cyclic peptide, and polymeric peptides A and B) were prepared in incomplete Freund's adjuvant as discussed above. These vaccines provided concentrations of peptide of 100 micrograms of peptide per inoculation.

Preliminary results of one inoculation in guinea pigs indicated a range of neutralization indices ($\log_{10}$) of about 2.3 to 3.0 for all three vaccines. The average neutralization index was about 2.5, indicating that each of the cystine disulfide-linked peptides protected the host against the Olk FMDV challenge.

A typical neutralization index value for the monomeric, unconjugated peptide whose sequence corresponds substantially to amino acid residue positions of about 141 to about 160 of Olk FMDV is approximately 0 5. These results therefore indicate that a carrier may not be needed to obtain protection in animals against foot-and-mouth disease.

IV. Carriers and Adjuvants

A. Alternative Carriers

The above results were obtained using inoculations of a KLH-peptide conjugate plus a physiologically acceptable diluent such as water along with adjuvants such as complete Freund's adjuvant (CFA), incomplete Freund's adjuvant (IFA) and/or aluminum hydroxide. KLH is an acceptable carrier for use in animals, but it is quite costly to use on a commercial scale. The use of alternative carriers including soybean agglutinin, bovine serum albumin (BSA), olvalbumin, peanut agglutinin, tetanus toxoid and poly-L-lysine was also examined.

The above results were also obtained by linking the antigenic peptide to the KLH molecule via an additional cysteine (Cys) residue added at the amino- or carboxy-terminus of the peptide. The Cys residue was then reacted with the reaction product of KLH and N-maleimidobenzoyl-N-hydroxysuccinimide ester (MBS), as discussed in Bittle et al., supra. Both MBS and glutaraldehyde were used as linking agents in the results discussed below. Linking of the synthetic peptide to KLH and BSA with glutaraldehyde was carried out following the general method of Avrameas, *Immunochemistry*, 6:13–52 (1969).

The results shown in Table 5 were obtained by linking a peptide of this invention having the amino acid sequence of positions 141–160 of the Olk FMDV VP1 capsid (peptide 65) to the carrier shown using MBS. Vaccines were prepared in incomplete Freund's adjuvant. Single inoculations containing sufficient conjugate to provide 100 micrograms of peptide were given subcutaneously to each of six guinea pigs. Peptide antibody titers shown are an average of the six values obtained four weeks after inoculation using the ELISA method of Bittle et al., supra.

TABLE 5

ANTIBODY RESPONSES TO PEPTIDE 65 COUPLED TO VARIOUS CARRIERS

| Carrier | Peptide Antibody Titer |
| --- | --- |
| Peptide 65 (no carrier) | 30 |
| KLH | 60 |
| KLH | 120 |
| Peanut agglutinin | 50 |
| Olvalbumin | 40 |
| Soybean agglutinin | <10 |
| Tetanus toxoid | 60 |
| Bovine serum albumin | 130 |

The above results illustrate that several carriers are almost as active as KLH, while bovine serum albumin provided a superior antibody titer.

Preliminary studies also showed that use of peptide 65 and tetanus toxoid with glutaraldehyde as linking agent provided a very good antibody response with one inoculation. For those linking reactions, a solution containing 24.5 milligrams of peptide 65 and 26 milligrams of tetanus toxoid in 12.5 milliliters of phosphate buffered saline (PBS, pH 7.2) was prepared. That solution was stirred gently while 1.6 milliliters of a solution containing 0.38 percent glutaraldehyde in PBS was admixed with it. The admixture was stirred for about 18 hours at room temperature, dialyzed against water in 12,000 molecular weight cut-off dialysis tubing, and then freeze dried to provide 45 milligrams of dried conjugate.

B. Adjuvants

Adjuvant systems were also examined using the above peptide 65-linked carriers. The results illustrates in Table 6 show the effects of varying the carrier between KLH and BSA, the couping agent between MBS and glutaraldehyde, and the adjuvant between incomplete Freund's adjuvant (IFA) and saponin-aluminum hydroxide, referred to in Table 6 as saponin. Each of six guinea pigs was inoculated subcutaneously with vaccines containing 100 micrograms of peptide 65 and the adjuvant in two inoculations, four weeks apart. The results are averaged values for the six animals and are reported as were the results of Table 5.

TABLE 6

ANTIBODY RESPONSES OF GUINEA PIGS TO PEPTIDE 65: COMPARISON OF CARRIERS, COUPLING AGENT AND ADJUVANT[1]

| Carrier | Coupling Method | Adjuvant | Weeks Post-immunization | | | |
| --- | --- | --- | --- | --- | --- | --- |
| | | | 4 | 8 | 12 | 20 |
| KLH | MBS | Saponin | 2.9 | 4.2 | 3.5 | — |
| | | | 255 | 1020 | 1060 | 400 |
| KLH | MBS | IFA | 3.1 | 3.5 | 2.5 | — |
| | | | 123 | 1024 | 550 | 435 |
| BSA | MBS | Saponin | — | — | — | — |
| | | | — | 730 | ≧640 | 145 |
| BSA | MBS | IFA | — | — | — | — |
| | | | — | 620 | 340 | 170 |
| KLH | Glutaraldehyde | Saponin | 2.5 | ≧4.7 | 4.0 | — |
| | | | 50 | 960 | ≧1056 | 1280 |
| KLH | Glutaraldehyde | IFA | 2.8 | 3.2 | 1.7 | — |
| | | | | 12 | 356 | 190 |
| BSA | Glutaraldehyde | Saponin | — | — | — | — |
| | | | — | 1024 | >800 | 480 |
| BSA | Glutaraldehyde | IFA | — | — | — | — |
| | | | — | <10 | 8 | 10 |

[1] Data in the first horizontal row under the heading "Weeks Post-immunization", for each vaccine are neutralization index (log 10) values, while the horizontal row thereunder contains peptide antibody titer data obtained from the ELISA technique. The data were taken as discussed in Bittle et al., supra.

The above data illustrate that saponinaluminum hydroxide provides a higher and more prolonged antibody response than incomplete Freund's adjuvant (IFA) regardless of whether the peptide was coupled with either glutaraldehyde or MBS, or whether the carrier was KLH or BSA.

The data in Table 7, below, show antibody titer responses and neutralization results, using the before described techniques, when peptide 65 coupled to KLH was used as the vaccine along with one of two adjuvant systems. The first horizontal row of data for each vaccine contains the neutralization index (log $_{10}$) values, while the horizontal row therebelow contains the peptide antibody titers obtained by ELISA.

TABLE 7
ANTIBODY RESPONSE OF GUINEA PIGS TO PEPTIDE 65-KLH CONJUGATE COMPARING TWO ADJUVANTS

| Dose (Micrograms) | Adjuvant | Weeks Post-immunization | | | |
|---|---|---|---|---|---|
| | | 5 | 12 | 16 | 20 |
| 200 | CFA[1] | >6.3 | >3.6 | >3.9 | >6.3 |
| | IFA | >1024 | >1024 | >2560 | 1280 |
| | Al(OH)₃ | | | | |
| 200 | Saponin[2] | >6.3 | >3.9 | >3.7 | 3.3 |
| | | >1024 | 960 | 240 | 480 |
| 1000 | Saponin[2] | 5.3 | >3.9 | >3.9 | 3.5 |
| | | 7680 | 240 | 200 | 240 |

[1]Peptide amount in dose using the three adjuvant system as described beneath Table 1 of Bittle et al., supra.
[2]Peptide amount of dose in saponin-aluminum hydroxide inoculated subcutaneously on days 0, 14 and 21.

The above results illustrate that vaccines containing the three adjuvant system provided greater amounts of antibodies for a longer duration than did the vaccines containing saponin-aluminum hydroxide. There also appeared to be little difference between the two dosages administered in saponin-aluminum hydroxide.

The data in Tables 8 and 9 illustrate responses in mixed breed cattle and swine to multiple inoculations of vaccine containing the peptide 65-KLH conjugate (MBS coupled) and saponin-aluminum hydroxide. Those results illustrate that both animal types respond to the synthetic antigenic peptides by developing antibodies at a level that is considered protective. In each Table, the first horizontal row of data for each animal are neutralization index (log 10) results, while the second horizontal row of data are peptide antibody titer values obtained by ELISA.

TABLE 8
ANTIBODY RESPONSE OF CATTLE TO PEPTIDE 65-KLH CONJUGATE[1]

| Animal # | Weeks Post-immunization | | | | | | |
|---|---|---|---|---|---|---|---|
| | 3 | 4 | 6 | 10 | 18 | 26 | 28 |
| 1 | 2.3 | 2.3 | 2.7 | — | 2.1 | — | >3.7 |
| | — | ≧1280 | ≧1280 | 480 | 40 | <10 | 30 |
| 2 | 3.3 | 3.3 | ≧3.9 | — | 2.1 | — | ≧3.7 |
| | — | >5120 | ≧5120 | 480 | 120 | <10 | 960 |
| 3 | 2.3 | ≧3.7 | 2.1 | — | 1.1 | — | ≧3.7 |
| | — | 120 | 120 | 10 | 10 | <10 | 10 |

[1]Vaccine composed of peptide 65 coupled to KLH with MBS to provide 2 milligrams of peptide in saponin-aluminum hydroxide per dose, and administered subcutaneously at 0, 3 and 26 weeks.

TABLE 9
ANTIBODY RESPONSE OF SWINE TO PEPTIDE 65-KLH CONJUGATE[1]

| Animal # | Weeks Post-immunization | | | | |
|---|---|---|---|---|---|
| | 3 | 4 | 5 | 13 | 26 |
| 1 | 1.7 | 2.1 | — | — | — |
| | 160 | 120 | 480 | 120 | 80 |
| 2 | 1.5 | 2.3 | — | — | — |
| | 240 | 240 | 480 | 30 | 10 |
| 3 | 2.3 | 3.1 | — | — | — |
| | 480 | 320 | 960 | 80 | 15 |

[1]Vaccine composed of peptide 65 coupled to KLH with MBS to provide 1 milligram of peptide in saponin-aluminum hydroxide per dose, and administered subcutaneously at 0, 3 and 26 weeks.

The above results in Table 8 with cattle illustrate an anamnestic response in that the six month booster inoculation triggered memory B cell production of neutralizing antibodies.

In a general sense, then, one aspect of the invention is a process for producing FMDV vaccines which have all of the immunizing effect of prior art vaccines but which are totally free of competing or cross referencing immunological side effects.

The results reported above as to inoculations with synthetic antigenic peptides of this invention were carried out using peptides of only one sequence for each set of data. The data in Table 3 show that some cross-reactivity and poly-specifity was observed.

In another embodiment of this invention cross-reactivity and poly-specificity are obtained by inoculations utilizing a plurality of peptides of this invention that are each mono-specific to at least a different strain of virus within a genus, or to different serotypes or strains within the genus. Thus, inoculation with a vaccine containing peptides of this invention whose amino acid residue sequences correspond substantially to amino residue positions about 141 to about 160 of both type 01k and type A, subtype 10, strain 61 (A10, 61) provides protection against both types 01K and A10, 61. Similarly, a polymeric peptide such as polymeric peptides A and B, discussed hereinbefore, may be prepared as a copolymeric peptide whose repeating peptide units are present in about equal amounts and have amino acid residue sequences corresponding substantially to amino acid residue positions about 141 to about 160 of Olk and A10, 61, respectively.

V. Polio Virus-related Synthetic Peptides

Several synthetic peptides have been prepared containing a sequence of about twenty amino acid residues each. Four of those sequences corresponded substantially to the amino acid sequences of the $VP_1$ capsid proteins of type 1 Mahoney and Sabin polio viruses and type 3 Leon virus in the regions of amino acid positions of about 61 to about 80 and about 182 to about 201. The $VP_1$ amino acid residue sequences Mahoney and Sabin strains of type 1 polio virus are identical in the above regions.

The sequences of those four, synthetic peptides are shown in FIG. 2. Those four sequences are shown below written as two synthetic peptide sequences of this invention denominated as PP1 and PP2 from left to right and in the direction from amino-terminus to carboxy-terminus, as follows:

PP1: ValGlnThrArgHisValValGlnHis(Arg)Arg-SerArgSerGlu SerSer(Thr)IleGluSerPhe, and PP2: SerIlePheTyrThrTyrGlyThr(Ala)Ala-ProAlaArgIleSer ValProTyrValGlyIle(Leu), wherein the parenthesized amino acid residues in each of the above sequences may independently replace the contiguous amino acid residue to the immediate left of the parentheses; i.e., the amino acid residue closer to the amino-terminus. For purposes of reference, the PP1 amino acid residue sequence can be seen to correspond substantially (as defined hereinbefore) to the amino acid residue sequence of positions about 61 to about 80 of the polio types 1 and 3 $VP_1$ capsid, while the PP2 amino acid residue sequence corresponds substantially to the amino acid residue sequence of positions about 182 to about 201 of the $VP_1$ capsid of polio viruses types 1 and 3.

Each of the above PP1 and PP2 amino acid residue sequences represents at least four peptides of this invention. The four synthetic, peptides of each region have the amino acid sequences shown below in the order written above, and designated PP1a, PP1b, PP1c, PP1d, as well as PP2a, PP2b, PP2c and PP2d, respectively:

PP1a: ValGlnThrArgHisValValGlnHisArgSerArg-
SerGlu SerSerIleGluSerPhe

PP1b: ValGlnThrArgHisValValGlnArgArgSerArg-
SerGlu SerSerIleGluSerPhe

PP1c: ValGlnThrArgHisValValGlnHisArgSerArg-
SerGlu SerThrIleGluSerPhe

PP1d: ValGlnThrArgHisValValGlnArgArgSerArg-
SerGlu SerThrIleGluSerPhe

PP2a: SerIlePheTyrThrTyrGlyThrAlaProAlaArg-
IleSer ValProTyrValGlyIle

PP2b: SerIlePheTyrThrTyrGlyAlaAlaProAlaArg-
IleSer ValProTyrValGlyIle

PP2c: SerIlePheTyrThrTyrGlyThrAlaProAlaArg-
IleSer ValProTyrValGlyLeu

PP2d: SerIlePheTyrThrTyrGlyAlaAlaProAlaArg-
IleSer ValProTyrValGlyLeu

VI. Experimental Procedures and Inoculations

Each of the four synthetic peptides of FIG. 2 was synthesized, as were several additional peptides corresponding to additional positions of the polio type 1 $VP_1$ capsid, following the procedures discussed hereinbefore for FMDV-related peptides and disclosed in Bittle et al, supra. Carboxy-terminal Cys residues were added for linking via MBS to KLH as carriers to form conjugates, following the previously described procedures. The conjugates whose sequences corresponded to type 1 capsid proteins were made into vaccines using the peptide amount per dose and three dose-three adjuvant system described above beneath Table 1 of Bittle et al., supra. Rabbits were the inoculated host animals.

Efficacy determinations were made by determining antibody serum dilutions that would provide 50 percent of the stationary culture tubes containing monolayer cell cultures with protection against infection with added type 1 polio virus. BSC-1 cells were grown in L-15 medium in 5% fetal bovine serum.

After the cultured cell monolayers were formed, the tubes were inoculated with a predetermined amount of live Sabin type 1 polio virus particles and antiserum from inoculated rabbits. The inoculated cultured cells were then examined along with appropriate controls two through eight days thereafter.

The polio virus particles were inoculated as multiples of a tissue culture infection dosage (TCID), a single dosage amount being sufficient to infect and kill 50 percent of similarly monolayered cultured cells ($TCID_{50}$) as determined before each series of determinations was made. The minimal $TCID_{50}$ for these determinations was 50; i.e., 50 times the $TCID_{50}$ of polio virus particles was used for the inoculation. Multiples of 50, 100, 900 and 1000 $TCID_{50}$ were used with serum dilutions of 1:8, 1:16, 1:32, 1:64, 1:128 and 1:256 to obtain the antiserum titer values following usual techniques.

At least four monolayer culture-containing wells or tubes were used per serum-virus dilution. One or two rabbits were inoculated with the various carrier-linked peptides following the above-described vaccination schedule. The results of these determinations are shown in Table 10, below.

TABLE 10

ANTIBODY NEUTRALIZATION TITERS OF POLIO TYPE 1 FROM DIFFERENT PEPTIDES IN CULTURED CELLS

| KLHL-Peptide Antigen[1] | Polio Virus Inoculation in Multiples of $TCID_{50}$ | | | |
|---|---|---|---|---|
|  | $50^2$ | $100^2$ | $900^2$ | $1000^2$ |
| 12–40 | 8 | —[3] | — | — |
| 61–80 | 48 | 27 | 18 | — |
| 86–103 | — | — | — | — |
| 121–140 | — | — | — | — |
| 161–180 | —, 14 | —, — | —, — | —, — |
| 182–201 | 40, 32 | 27, 25 | 13, 20 | 11, 13 |
| 202–222 | —, — | —, — | —, — | —, — |
| 244–264 | —, — | —, — | —, — | —, — |
| 265–285 | —, — | —, — | —, — | —, — |
| 286–301 | 16, 13 | 10, 8 | —, — | —, — |

[1] The numbers refer to the amino acid residue position of the Mahoney type 1 $VP_1$ capsid from the amino-terminus to which the amino acid residue sequences of the synthetic peptides substantially correspond.
[2] Titers are given as dilutions of serum required to provide 50% protection for each $TCID_{50}$ multiple. A titer of 8 therefore means that a 1 to 8 dilution of the serum provided the required protection, etc.
[3] The presence of dashes in this Table indicates that the titer was less than 1:8. Two titer entries indicate that two rabbits were inoculated with a vaccine containing the indicated peptide.

The above data illustrate that there are two antigenic determinant domains on the polio type 1 $VP_1$ capsid. Those determinant domains are located at about amino acid residue positions 61 to about 80, and at about positions 182 to about 201, respectively. The data also show that the peptide corresponding substantially to positions about 182 to about 201 provided protection at a higher concentration of virus than did the other peptide.

VII. Synthetic Peptides Related to Picornaviruses

The before-described results with FMDV and polio virus antigenic capsid proteins represent two specific embodiments of a broader invention that relates to the family of Picornaviruses generally, rather than to two specific genera, the FMDV and polio virus. That broader invention relates to synthetic antigenic peptides that each contain a sequence of about 20 amino acid residues that at least corresponds in amino acid residue sequence to a region on the antigenic Picornavirus capsid protein that is found about 60 to about 75 percent of the amino acid residue sequence length from the amino-terminus of that antigenic capsid protein. Those synthetic peptides are and bear a neutral, or more preferably a positive net ionic change at physiological pH values, exclusive of any charge that might be due to terminal carboxyl or alpha-amino groups. The presence of a net neutral or positive charge can be readily determined by electrophoresis determinations at physiological pH values or from examination of the amino acid residue sequence and a knowledge of $pK_a$ values for the individual amino acid residues.

The above synthetic, peptides can be used alone, as a polymer wherein the peptide units are linked together by oxidized cysteine residues, or linked to a carrier as a conjugate along with physiologically tolerable diluents such as water or an adjuvant to provide a vaccine which, when introduced into a host in an effective amount is capable of inducing the production of antibodies that react with the Picornavirus to whose capsid protein sequence the peptide corresponds or corresponds substantially and protect that host from that Picornavirus. This synthetic, peptide, alone, as a polymer or conjugate can also be used as discussed hereinbefore or hereinafter for the about 20 amino acid residue-containing peptides whose sequences correspond or correspond substantially to the amino acid residue sequence of positions about 130 to about 160 from the amino-terminus of the FMDV VP$_1$ capsid.

In examining the active antibody-inducing regions of the antigenic Picornovirus capsid it is noted that one determinant region of FMDV VP$_1$ to which neutralizing anitbodies may be raised corresponds to amino acid residue positions of about 130 through about 160 from the amino terminus of the capsid. The VP$_1$ capsid includes a total of about 213 amino acid residues from amino-terminus to carboxy-terminus, using the Olk virus VP$_1$ as the reference protein.

Thus, the region of the protein at which the neutralizing antibody determinant begins is located about 60 percent ($130/213 \times 100\% = 61\%$) of the way down the amino acid residue sequence of that protein from the amino-terminus. That neutralizing antibody-producing determinant region ends at about amino acid residue position 160 which represents about 75% of the amino acid residue sequence from the amino-terminus. For the more preferred peptides corresponding substantially to amino acid residue positions of about 141 through about 160 of the FMDV VP$_1$ capsids, the neutralizing antibody-producing determinant region is within the region located at a distance from the amino-terminus equal to about 66 to about 75 percent of the total amino acid residue sequence.

Examining the data for the type 1 polio virus, above, it is seen that conjugates containing peptides whose sequences correspond substantially to the region of capsid amino acid residue positions of about 182 through about 201 from the amino-terminus are major producers of neutralizing antibodies against that virus. The synthetic peptide thereby defines the neutralizing antibody-producing determinant region of the type 1 polio virus.

The antigenic capsid of the type 1 polio virus contains a total 302 amino acid residues in its sequence. A neutralizing antibody-producing determinant of the type 1 polio virus is therefore located in the region of about 60 through about 66 percent of the amino acid residue sequence of that antigenic capsid from the amino-terminus, calculated as above.

Examination of the amino acid residue sequences in FIGS. 1 and 2 and of the readily available appropriate pK$_a$ data reveals that the number of residues in each sequence that would bear a positive ionic charge at physiological pH values (Arg, Lys and His) outnumbers the number of residues that would bear a negative charge at that pH value (Asp and Glu) for all sequences but one. That one sequence, of FMDV type A, subtype 10, strain 61 (A10, 61), bears a neutral ionic charge. It is noted, however, that the particularly preferred region of the A10 capsid corresponding substantially to amino acid residue positions about 141 to about 160 bears a net positive charge.

The synthetic antigenic peptides of this invention typically bear a net neutral or positive charge, exclusive of any inoic charges caused by terminal amino and/or carboxyl groups. Preferably, these peptides bear a net positive ionic charge. Such peptides are also preferably water-soluble. It appears, however, that the net neutral to positive charge on the synthetic antigenic peptide is not as important to the peptide's antigenicity as is the fact that the peptide's amino acid residue sequence at least corresponds to a region on the antigenic neutralizing antibody-inducing capsid that is between about 60 and 75 percent of the length of that sequence from the amino-terminus.

VIII. Diagnostics

The method of the invention may be used in the preparation of diagnostic tests, such as immunoassays, in which it is necessary to have antibodies to the organism to be detected or a synthetic antigen mimicking a determinant on the organism to be detected. Such diagnostic techniques include, for example, enzyme immune assay, radioimmune assay, fluorescence immune assay, and other techniques in which either the antibody or the antigen is labelled with some detectable tag.

For example, using the double antibody technique outlined by Voller, et al., "Enzyme Immune Assays in Diagnostic Medicine", *Bulletin of the World Health Organization,* Volume 53, pp. 55-65 (1976), an ELISA test may be used in the preparation of diagnostic tests.

A double antibody ELISA was used in obtaining the above-discussed anti-peptide antibody titer data, and those data reported in Table 1 of Bittle, et al. supra. Specifics for that ELISA are provided beneath Table 1 of that Bittle et al. report, supra.

A diagnostic system of this invention for assaying for the presence of a Picornavirus antigen contains the antibodies raised to a peptide of this invention present in biologically active form along with a means for indicating the presence of an iommunoreaction. When admixed with a body component such as serum, urine or a tissue extract, the antibodies immunoreact with the Picornavirus antigen to form an immunoreactant, and the indicating means signals that immunoreaction.

For example, the body component may be coated on an ELISA test well and incubated with the antibodies of this invention such as those raised in rabbits, following well known techniques. After rinsing away any un-immunoreacted antibodies, a second, enzyme-linked second antibody raised to the first type of antibody such as goat-antirabbit antibodies containing linked alkaline phosphatase is admixed and incubated in the ELISA well. Any excess of the second antibodies is rinsed out leaving any phosphatase-linked goat-antirabbit antibodies that bound to an antibody of this invention within the ELISA well. Subsequent admixture of an enzyme substrate such as p-nitrophenyl phosphate provides the signal that an immunoreactant was formed, and therefore that a Picornavirus antigen was present in the body component.

A radioactive element such as $^{125}$I may be bonded to an antibody of this invention to provide the incubating means. Here, for example, the body component may be precoated in a sample tube followed by incubation with the radioactive antibodies and rinsing of excess antibodies from the tube. Radioactivity remaining in the tube after rinsing provides the signal that an immunoreactant was formed.

Another embodiment of this invention contemplates a diagnostic system for assaying for the presence of a Picornavirus antigen in a body component such as those discussed before. This system is particularly useful in competition assays and includes a first reagent and a second reagent in separate containers.

The first reagent contains a synthetic, antigenic peptide of this invention in biologically active form. The second reagent contains antibodies in biologically active form that immunoreact with that peptide such as those raised to the peptide. A means for indicating the presence of an immunoreaction between the peptide and antibodies such as discussed hereinbefore is also included either in a separate container as in phosphatase-linked goat-antirabbit antibodies and its substrate, or along with the antibodies as where radioactive elements are bonded to the antibodies.

Admixture of predetermined amounts of the first and second reagents in the presence of a predetermined amount of body component to be assayed provides an amount of immunoreaction signalled by the indicating means. The amount of the immunoreaction is different from a known amount of immunoreaction when a Picornavirus antigen is present in the body component.

In usual practice, the body component is pre-incubated with the antibody and that composition is then incubated with the peptide that is bound to the walls of an ELISA well. Rinsing of the well to remove any antibody-Picornavirus antigen complex leaves an immunoreactant of the peptide and antibody whose presence and amount may be signalled by the indicating means.

The use of whole, intact, biologically active antibodies is not necessary in many diagnostic systems such as the competition assay discussed immediately above. Rather, only the biologically active idiotype-containing, antigen binding and recognition portion of the antibody molecule may be needed. Illustrative of the idiotype-containing antibody portions are those known as Fab and F(ab')2 antibody portions that are prepared by well known enzymatic reactions on typically whole antibodies.

Whole, intact antibodies, Fab, F(ab')2 portions and the like that contain the antibodies' idiotypic regions are denominated herein as idiotype-containing polyamides. The phrase "idiotype-containing polyamide" is used in the appended claims to embrace the group of such molecules as are useful in diagnostic products or techniques. However, while Fab or F(ab')2 antibody portions may be utilized as the idiotype-containing polyamide of a diagnostic technique or product, use of the whole, intact antibody is usually preferred, if only because preparation of an Fab or F(ab')2 portion of an antibody requires additional reaction and purification of sera.

IX. Methods and Art

Methods and materials unique to this invention are described with reference to the particular proceudre under consideration. In general, however, the laboratory techniques, methods and materials utilized are those commonly used in molecular biology and biochemistry generally.

Particular reference is made to *METHODS IN ENZYMOLOGY*, Colowick, S. P. and Kaplan, N. O., Editors, Academic Press, New York; *METHODS IN IMMUNOLOGY AND IMMUNOCHEMISTRY*, Academic Press, *HANDBOOK OF BIOCHEMISTRY AND MOLECULAR BIOLOGY*, Chemical Rubber Publishing Company, and *CELL BIOLOGY: A COMPREHENSIVE TREATISE*, Goldstein and Prescott, Academic Press, N.Y., N.Y. for a description of a reference to the general materials and techniques of interest.

The following references disclose particular steps and techniques known in the art and the current state of the art as well.

References

1. Baltimore, D., Cold Spring Harbor Symp., *Quant. Biol.* 39, 1187–1200 (1974).
2. Oskarsson, M. K., Elder, J. H., Gautsch, J. W., Lerner, R. A. and Vande Woude, G. F., *Proc. Natl. Acad. Sci.*, U.S.A. 75, 4694–4698 (1978).
3. Gautsch, J. W., Elder, J. H., Schindler, J., Jensen, F. C., and Lerner, R. A., *Proc. Natl. Acad. Sci.*, U.S.A. 75, 4170–4174 (1978).
4. Jamjoon, G. A., Naso, R. B. and Arlinghaus, R. B., *Virol.* 78, 11–34 (1977).
5. Famulari, N. C., Buchhagen, D. L., Klenk, H. D., and Fleissner, E., *J. Virol.* 20, 501–508 (1976).
6. Witte, O. N., Tsukamoto-Adey, A. and Weissman, L. L., *Virol.* 76, 539–553 (1977).
7. Fan, H. and Verma, I. M., *J. Virol.* 26, 468–478 (1978).
8. Sutcliffe, J. G., Shinnick, T. M., Lerner, R. A., Johnson, P. and Verma, I. M., Cold Spring Harbor Symp. *Quant. Biol.* 44, in press (1979).
9. Sutcliffe, J. G., Shinnick, T. M., Verma, I. M. and Lerner, R. A., *Proc. Natl. Acad. Sci.*, U.S.A. in press (1980).
10. Marglin, A. and Merrifield, R. B., *Ann. Rev. Biochem.* 39, 841–866 (1970).
11. Pederson, F. S. and Haseltine, W. A., *J. Virol.* 33, 349–365 (1980).
12. *Atlas of Protein Sequence and Structure*, Vol. 5, Sup. 3, M. O. Dayhoff, ed., Natl. Biomed, Res. Found., pub. Washington, D.C. (1978).
13. Dayhoff, M. O., Schwartz, R. M. and Orcutt, B. C., pp. 352, op. cit.
14. Fisher, R. A., *The General Theory of Natural Selection*, Clarendon Press, Oxfore (1930).
15. Elder, J. H., Gautsch, J. W., Jensen, F. C., Lerner, R. A., Harley, J. W. and Rowe, W. P., *Proc. Natl. Acad. Sci.*, U.S.A. 74, 4676–4680 (1977).
16. Lerner, R. A., Jensen, F. C., Kennel, S. J., Dixon, F. J., Roches, G. D. and Francke, U., *Proc. Nat. Acad. Sci.*, U.S.A. 69, 2965–2969 (1972).
17. Niman, H. L. and Elder, J. H., *Proc. Nat. Acad. Sci.*, U.S.A., in press (1980).
18. Edwards, S. A. and Fan, H., *J. Virol.* 30, 551–563 (1979).
19. Kitagawa, T. and Ailawa, T., *J. Biochem. (Tokyo)* 79, 233 (1976).
20. Liu, F., Zinnecker, M., Hamaoka, T. and Katz, D. H. *Biochem.* 18, 690 (1979).
21. Katz, David H., U.S. Pat. No. 4,191,668, Mar. 4, 1980.
22. *J. Exp. Med.*, 134: 201–203 (1971).
23. *J. Exp. Med.*, 136: 426–438, 1404–1429 (1972).
24. *J. Exp. Med.*, 138: 312–317 (1973).
25. *J. Exp. Med.*, 139: 1446–1463 (1974).
26. *Proc. Natl. Acad. Sci.*, U.S.A., 71: 3111–3114.
27. *Proc. Natl. Acad. Sci.*, U.S.A., 73: 2091–2095 (1976).
28. *J. Immunol.* 144: 872–876 (1975).
29. *J. Immunol.* 120: 1824–1827 (1978).
30. *J. Exp. Med.*, 139: 1464–1472 (1974).
31. Humphrey, J. H. and White, R. G., *Immunology for Students of Medicine*, Blackwell, Oxford (1970).
32. Katz, David H. and Benacerraf, Baruj, *Immunological Tolerance, Mechanisms and Potential Therapeutic Applications*, Academic Press (1974).
33. *Newsweek*, Mar. 17, 1980, pp. 62–71.
34. *Chemical & Engineering News*, June 23, 1980, p. 10.
35. Milstein, C., *Differentiation* 13: 55 (1979).
36. Howard, J. C., Butcher, G. W., Galfre', G., Milstein, C. and Milstein, C. P., *Immunol. Rev.* 47: 139 (1979).
37. Hammerling, G. J., Hammerling, U., and Lemke, H., *Immunogenetics* 8: 433 (1978).

38. Shulman, M., Wilde, C. D., and Kohler, G., *Nature* 276: 269 (1978).
39. Kohler, G. and Milstein, G., *Nature* 256: 495 (1975).
40. Ledbetter, J. A. and Herzenberg, L. A., *Immunol. Rev.* 47: 63 (1979).
41. Gefter, M. L., Margulies, D. H. and Scharff, M. D., *Somatic Cell Genetics* 3: 231 (1977).
42. Kohler, G. and Milstein, C., *Eur. J. Immunol.* 6: 511 (1976).
43. *J. Biol. Chem.*, 241: 2491-2495 (1966).
44. *J. Biol. Chem.*, 241: 555-557 (1967).
45. Koprowski, Hilary et al., U.S. Pat. No. 4,196,265, April 1980.
46. *Science* 209, No. 4463, pp. 1319-1438 (September 1980 - entire numberr).
47. Davis, B. D., Dulbecco, R. Eisen, H. N., Ginsbert, H. S., Wood, W. B. Jr., and McCarty, M., *Microbiology*, Harper & Row, Hagerstown, Md., 1973.
48. Morgan, J. and Whelan, W. J., *Recombinant DNA And Genetic Experimentation*, Pergamon Press, New York, 1979.
49. Goldstein, L. and Prescott, D. M., *Cell Biology, A Comprehensive Treatise* Vols. 1, 2 & 3, Academic Press, San Francisco.
50. Scott, W. A. and Werner, R., *Molecular Cloning of Recombinant DNA*, Academic Press, New York, 1977.
51. Wu, Ray (Ed.), Colowick, Sidney P., and Kaplan, Nathan O., *Methods in Enzymoloqy*, generally and Vol. 68, "Recombinant DNA" in particular, Academic Press, New York.
52. Cooper, Terrance G., *The Tools of Biochemistry*, John Wiley & Sons, New York, 1977.
53. Sela, Michael, *Science* 166: 1365-1374 (1969).
54. Arnon, R., Elchanan, M., Sela, M. and Anfinsen, C. B., *Proc. Natl. Acad. Sci. U.S.A.*, 68: 1450 (1971).
55. Sela, M., *Adv. Immun.* 5: 29-19 (1966).
56. Sela, M., Arnon, R., and Chaitchik, S., U.S. Pat. No. 4,075,194, Feb. 21, 1978.
57. Cohen, S. N., and Boyer, H. W., U.S. Pat. No. 4,237,224, Dec. 2, 1980.
58. Lerner, R. A., Sutcliffe, J. G. and Shinnick, T. M. (1981) *Cell* 23: 109-110.
59. Wilson, I. A., Skehel, J. J. and Wiley, D. C. (1981), *Nature* 289: 366-373.
60. Sutcliffe, J. G., Shinnick, T. M., Green, N., Liu, F-T, Niman, H. L., and Lerner, R. A. (1980), *Nature* 287: 801-805.
61. Kleid, D. G., Yansura, D., Small, B., Dowbenko, D., Moore, D. M., Grubman, M. J., McKercher, P. D., Morgan, D. O., Robertson, B. H., Bachrach, H. L., *Science* 214: 1125-1129 (1981).
62. CELL BIOLOGY, A COMPREHENSIVE TREATISE, Goldstein, L., and Prescott, D. M., Eds., Academic Press, N.Y., 1977 et. seq.
63. MOLECULAR BIOLOGY OF THE GENE, 3rd Ed., Watson, J. D., W. A. Benjamin, Inc., Menlo Park, Calif. 1977.
64. *Scientific American*, "Recombinant DNA" W. H. Freeman and Company, San Francisco 1978.
65. Nofschneider, P., Heinz, S., Kupper, H. A., Keller, W., UK Patent Application GB No. 2 079 288 A, published Jan. 20, 1982.
66. Kupper, H., Keller, W., Kunz, C., Forss, S., Scholler, H., Franze, R., Strohmair, K., Marquardt, O., Zaslovsky, V. G., and Hofschneider, P. H., "Cloning of cDNA of major antigen of foot and mouth disease virus and expression in *E. Coli.*," *Nature* 289: 555-559 (1981).
67. Walter, G., Scheidtmann, K., Carbone, A., Laudano, A. P., Doolittle, R. F., *Proc. Natl. Acad. Sci. USA* 77: 5197-5200 (1980).
68. Fracastorius, H. DeContagione et Contagiosis morbis et Curatione, Libri iii. (1546)
69. King., A. M. Q., Underwood, B. O., McCahon, D., Newman, J. W. I. and Brown, F. Nature, 293, 479-480 (1981).
70. Cooper, P. D. et al. Intervirology 10, 165-180 (1978).
71. Wild, T. F., Burroughs, J. N. and Brown, F., J.Gen. Virol. 4, 313-320 (1969).
72. Laporte, J., Grosclaude, J., Wantyghem, J., and Rouze, P., C.r. hebd. Acad.Sci.Seanc. Paris, 276, 3399-3401 (1973).
73. Bachrach, H. L., Moore, D. M., McKercher, P. D. and Polatnick, J., J. Immun. 115, 1636-1641 (1975).
74. Kaaden, O. R., Adam, K-H, and Strohmaier, K., J.Gen. Virol. 34, 397-400 (1977).
75. Melven, R. H., Rowlands, D. J. and Brown, F., J.Gen. Virol. 45, 761-763 (1979).
76. Boothroyd, J. C. et al. Nature 290, 800-802 (1981).
77. Boothroyd, J. C., Harris, T. J. R., Rowlands, D. J. and Lowe, P. A. Gene (in press).
78. Kurz, C., Forss, S., Kupper, H., Strohmaier, K. and Schaller, H., Nucleic Acids Res. 9, 1919-1931 (1981).
79. Strohmaier, K., Franze, R. and Adam, K-H. Proc. 5th Int. Congress Virology, Strasbourg (1981).
80. Houghten, R. A., Chang, W. C. and Li, C. H., Int.J-.Pept.Prot.Res. 16, 311-320 (1980).
81. Houghten, R. A. and Li, C. H., Anal.Biochem. 98, 36-46 (1979).

X. Conclusion

Lerner et al, have been working on FMDV for a long period of time and, for a period, considered that they had identified the optimum specific antigenic determinant peptide fragment for FMDV, only to find that the supposed antigenically active portion did not induce the production of antibodies to FMDV, or induced antibody production at such low levels as to be of little or no practical value. We were aware that Strohmaier, et al., supra, had drawn some inferences as to antigenically active portions of their $VP_{Thr}$ ($VP_1$) FMDV serotype O gene and that Kelid et al. had determined the nucleotide sequence of the $VP_3$ ($VP_1$) FMDV sterotype A, subtype 12 gene [*Science,* 214:1125-1129 (1981)]. It was, of course, impossible to determine from the nucleotide sequences which peptide fragment or fragments would be antigenic and, in particular, it was impossible to predict, or even make a guess, as to which peptide fragments would have optimum antigenicity for FMDV virus. As has been demonstrated above, the antibody-inducing region of the Olk $VP_1$ capsid predicted by Strohmaier et al., supra, was found to be much less active than the relatively longer region claimed herein and including regions predicted by Strohmaier et al. to be non-inducing of protective antibodies.

A number of peptides were synthesized, attached to carrier, e.g. KLH, and the resulting antigens were injected into animals. Antibodies from the animals were then challenged with FMDV to determine if the antigen was antigenically efficacious in inducing antibodies to the infectious organism.

It was a totally unexpected discovery that such a compartively small peptide fragment in the region of capsid positions about 130 to about 160, e.g. about a 20 residue long peptide, such as the sequence corresponding to positions about 141 to about 160, was extremely antigenic. It is, of course, impossible to determine whether or not there may be other and possibly even more antigenic nucleotide sequences in the FMDV gene, although there is no reason to predict that such would exist. An about 20 amino acid residue sequence from the VP$_1$ capsid 130–160 amino acid residue sequence according to this discovery, quite unpredictably and quite suprisingly, seems to be the optimum and probably the ultimate, give or take one or two (perhaps three) amino acid residues, FMDV mono-specific synthetic antigenic determinant peptide.

It is not presently known how much one can deviate from the exact peptide without losing the highly unexpected activity and efficacy of the vaccine or antigen of which the determinant is the FMDV mono-specific synthetic antigenic determinant; however, it is known from experience that (1) the peptide can be lengthened by a few amino acid units, (2) that at least one or two, perhaps up to four or five substitutions can be made, and (3) that the peptide sequence can be shortened slightly, probably by two or three, perhaps four, without losing the uniqueness of the invention. Such nonsubstantial deviations are known, in principle, to be possible without departing from the concept which has been described and the discovery which has been made. Thus, such minor variations are to be regarded as mere equivalent variants of the invention.

Our results show clearly that a single innoculation of the synthetic peptide constituted by about twenty amino acid residues in the 130–160 region, e.g. region 141–160, elicits sufficient virus neutralizing antibody to protect against a challenge with the virus. The protection afforded by the peptide is several orders of magnitude greater than the best results obtained by immunization with the capsid protein VP$_1$, irrespective of whether this is produced by disruption of virus particles or by expression in *E. coli* cells. Indeed, it is postulated that a small free peptide may be able to adopt a conformation approximating that it takes up in the virus particle, a situation not likely when it is constrained by the neighboring amino acid residues in an improperly folded VP$_1$. An alternative explanation is that immunodominant regions of VP$_1$ may be buried in the virus and are irrelevant for neutralization.

One clear advantage of the synthetic peptide of the present invention is its activity in eliciting a protective antibody response by a single innoculation. This good response to a single innoculation is very important because successful immunization against foot-and-mouth disease in the field depends on the vaccines being sufficently active to produce a protective response with one innoculation. Indeed preliminary work in cattle and pigs shows that the synthetic peptide can elicit an antibody response suffecent to protect these species against the disease.

Industrial Application

The diagnostic and therapeutic applications of the antigens of this invention, and the vaccine and antibody preparations thereof are of great industrial and economic value. Animals, such as swine and cattle, and including man, can be protected against the ravages of Picornavirus-induced diseases such as foot-and-mouth disease and polio thus increasing the supply of food and, importantly, of protein for the human population, and freeing man from the occurance of a crippling disease.

The foregoing is intended as illustrative of the present invention but not limiting. Numerous variations and modifications may be effected without department from the true spirit and scope of the novel concepts of the invention. It is to be understood that no limitation with respect to the specific peptides, antibodies, their compositions and uses illustrated herein is intended or should be inferred. The invention is defined by the claims which follow.

What is claimed is:

1. A synthetic, antigenic peptide of about twenty amino acid residues having a sequence that corresponds to an amino acid residue sequence of a region on the antigenic VP1 Picornavirus capsid protein located away from the amino-terminus of said antigenic capsid protein at a distance equal to about 60 to about 75 percent of the amino acid sequence length thereof; said peptide, when linked to a keyhole limpet hemocyanin carrier as a conjugate and introduced in an effective amount as a vaccine into a host animal, being capable of inducing production of antibodies in the host that immunoreact with said Picornavirus and protect the host from infection caused by said Picornavirus.

2. The synthetic peptide according to claim 1 having a net positive ionic charge, exclusive of ionic charges of terminal peptidal amino and/or carboxyl groups.

3. The synthetic peptide according to claim 1 wherein said Picornavirus is foot-and-mouth disease virus.

4. The synthetic peptide according to claim 1 wheren said Picornavirus is polio virus.

5. A synthetic, antigenic peptide of about twenty amino acid residues having a sequence corresponding to an amino acid residue sequence of the polio virus VP1 capsid protein from about position 61 to about 80 from the amino-terminus thereof; said peptide, when linked to a keyhole limpet hemocyanin carrier as a conjugate and introduced in an effective amount as a vaccine into a host animal, being capable of inducing production of antibodies in the host that immunoreact with said polio virus and protect the host from infection caused by said virus.

6. The synthetic peptide according to claim 5 the amino acid residue sequence of said peptide corresponds to that of a member of the group of amino acid residue sequences, written from left to right and in the direction from amino-terminus toward carboxy-terminus, consisting of:
ValGlnThrArgHisValValGlnHis(Arg)ArgSerArgSer GluSerSer(Thr)IleGluSerPhe,
wherein each of the amino acid residues in parentheses may individually replace the contiguous amino acid residue to the immediate left of the parentheses.

7. The synthetic peptide according to claim 5 wherein the amino acid residue sequence of said peptide corresponds to that of a member of the group of amino acid residues sequences, written from left to right and in the direction from amino-terminus toward carboxy-terminus, consisting of:
(1) ValGlnThrArgHisValValGlnHisArgSerArgSer GluSerSerIleGluSerPhe;
(2) ValGlnThrArgHisValValGlnArgArgSerArgSer GluSerSerIleGluSerPhe;
(3) ValGlnThrArgHisValValGlnHisArgSerArgSer GluSerThrIleGluSerPhe; and (4) ValGlnThrArgHisValValGlnArgArgSerArgSer GluSerThrIleGluSerPhe.

8. A synthetic, antigenic peptide containing a sequence of about twenty amino acid residues corresponding to an amino acid residue sequence of the polio virus VP$_1$ capsid protein, from about position 182 to about position 201 from the amino-terminus thereof; said peptide, when linked to a keyhole limpet hemocyanin carrier as a conjugate and introduced in an effective amount as a vaccine into a host animal, being capable of inducing production of antibodies in the host that immunoreact with said polio virus and protect the host from infection caused by said virus.

9. The synthetic peptide according to claim 8 wherein the amino acid residue sequence of said peptide corresponds to that of a member of a group of amino acid residue sequences, written from left to right and in the direction from amino-terminus toward carboxy-terminus, consisting of:
SerIlePheTyrThrTyrGlyThr(Ala)AlaProAlaArgIle SerValProTyrValGlyIle(Leu),
wherein each of the amino acid residues in parentheses may individually replace the contiguous amino acid residue to the immediate left of the parentheses.

10. The synthetic peptide according to claim 8 the amino acid residue sequence of said peptide corresponds to that of a group of amino acid residue sequences, written from left to right and in the direction from amino-terminus toward carboxy-terminus,
(1)  SerIlePheTyrThrTyrGlyThrAlaProAlaArgIleSerValProTyrValGlyIle
(2)  SerIlePheTyrThrTyrGlyAlaAlaProAlaArgIleSerValProTyrValGlyIle
(3)  SerIlePheTyrThrTyrGlyThrAlaProAlaArgIleSerValProTyrValGlyLeu
(4)  SerIlePheTyrThrTyrGlyAlaAlaProAlaArgIleSerValProTyrValGlyLeu 11. An antigenic polymer having repeating units comprising a plurality of antigenic peptides each having about twenty amino acid residues corresponding in sequence to an amino acid residue sequence of a region on the antigenic VP1 Picornavirus capsid protein that is located away from the amino-terminus of said antigenic capsid protein at a distance equal to about 60 and about 75 percent of the total amino acid sequence length thereof; said peptide, when linked to a keyhole limpet hemocyanin carrier as a conjugate and introduced in an effective amount as a vaccine into a host animal being capable of inducing production of antibodies in the host that immunoreact with said Picornavirus and protect the host from infection caused by said Picornavirus, said peptide repeating units being bonded together by oxidized cysteine residues to form said polymer.

12. The polymer according to claim 11 wherein said bonding, oxidized cysteine residues are joined in un-oxidized form to the amino- and carboxy-termini of each of said peptides by amide linkages prior to the polymerization of said peptide repeating units.

13. The polymer according to claim 11 wherein each of said plurality of peptides contains an amino acid sequence corresponding to an amino acid residue sequence of more than one strain of one genus of Picornaviruses.

14. A cyclic ring antigenic peptide of about twenty amino acid residues having a sequence corresponding to an amino acid residue sequence of a region on the antigenic VP1 Picornavirus capsid protein that is located away from the amino-terminus of said antigenic capsid protein at a distance equal to about 60 and about 75 percent of the total amino acid sequence length thereof; said peptide, when linked to a keyhole limpet hemocyanin carrier as a conjugate and introduced in an effective amount as a vaccine into a host animal, being capable of inducing production of antibodies in the host that immunoreact with said Picornavirus and protect the host from infection caused by said Picornavirus, the ends of said peptide bonded by oxidized cystein residues to form said cyclic ring.

15. The cyclic ring peptide according to claim 14 wherein said bonding, oxidized cysteine residues are joined in un-oxidized form to the amino- and carboxy-termini of each of said peptides by amide linkages prior to the cyclization of said peptide.

16. The cyclic ring peptide according to claim 14 wherein said cyclic ring includes at least two of said peptides bonded by oxidized cysteine residues.

17. A vaccine against infection by Picornaviruses comprising an effective amount of a synthetic, antigenic peptide of about twenty amino acid residues having a sequence corresponding to an amino acid residue sequence of a region on the antigenic VP1 Picornavirus capsid protein that is located away from the amino-terminus of said antigenic capsid protein, at a distance equal to about 60 and about 75 percent of the total amino acid sequence length thereof, and a physiologically tolerable diluent; said vaccine, when introduced into a host animal, being capable of inducing production of antibodies in the host that immunoreact with said Picornavirus and protect the host from infection caused by said Picornavirus.

18. The vaccine according to claim 17 wherein said synthetic peptide has a net positive ionic charge, exclusive of ionic charges of terminal peptide amino and/or carboxyl groups.

19. The vaccine according to claim 17 wherein said Picornavirus is foot-and-mouth disease virus.

20. The vaccine according to claim 19 wherein the amino acid residue sequence of said peptide corresponds to an amino acid residue sequence of the VP$_1$ capsid protein of said virus from about position 141 to about position 160 from the amino-terminus thereof.

21. The vaccine according to claim 17 wherein said Picornavirus is polio virus.

22. The vaccine according to claim 21 wherein the amino acid residue sequence of said peptide corresponds to an amino acid residue sequence of the VP$_1$ capsid protein of said virus from about position 182 to about 201 from the amino-terminus thereof.

23. The vaccine according to claim 17 wherein said physiologically tolerable diluent is a member of the group consisting of water and an adjuvant.

24. The vaccine according to claim 17 wherein said synthetic peptide is linked to a carrier.

25. The vaccine according to claim 24 wherein said carrier is selected from the group consisting of keyhole limpet hemocyanin, soybean agglutinin, bovine serum albumin, olvalbumin, peanut agglutinin, tetanus toxoid, poly-L-lysine and poly-L-(Lys:Glu).

26. The vaccine according to claim 17 wherein said synthetic peptide is present in the form of repeating units of a polymer, said peptide repeating units being bonded together to form said polymer by oxidized cysteine residues.

27. The vaccine according to claim 17 wherein said synthetic peptide is present in the form of a cyclic ring, the ends of said peptide being bonded by oxidized cysteine residues to form said cyclic ring.

* * * * *